(12) United States Patent
Wu et al.

(10) Patent No.: US 9,359,344 B2
(45) Date of Patent: Jun. 7, 2016

(54) BIARYL HETEROCYCLE SUBSTITUTED OXAZOLIDINONE ANTIBACTERIAL AGENTS

(71) Applicant: Xuanzhu Pharma Co., Ltd., Shandong (CN)

(72) Inventors: Frank Wu, Shandong (CN); Aichen Wang, Shandong (CN)

(73) Assignee: Xuanzhu Pharma Co., Ltd., Shondong (CN)

( * ) Notice: Subject to any disclaimer, the term of this patent is extended or adjusted under 35 U.S.C. 154(b) by 0 days.

(21) Appl. No.: 14/347,583

(22) PCT Filed: Sep. 28, 2012

(86) PCT No.: PCT/CN2012/082318
§ 371 (c)(1),
(2) Date: Mar. 26, 2014

(87) PCT Pub. No.: WO2013/044845
PCT Pub. Date: Apr. 4, 2013

(65) Prior Publication Data
US 2014/0235584 A1     Aug. 21, 2014

(30) Foreign Application Priority Data
Sep. 29, 2011 (CN) .......................... 2011 1 0290839

(51) Int. Cl.
| | |
|---|---|
| *C07D 401/14* | (2006.01) |
| *C07D 417/14* | (2006.01) |
| *C07D 413/14* | (2006.01) |
| *A61K 31/4439* | (2006.01) |
| *C07F 9/6558* | (2006.01) |
| *A61K 31/04* | (2006.01) |

(52) U.S. Cl.
CPC .............. *C07D 417/14* (2013.01); *A61K 31/04* (2013.01); *A61K 31/4439* (2013.01); *C07D 413/14* (2013.01); *C07F 9/65583* (2013.01)

(58) Field of Classification Search
CPC ........................... C07D 401/14; C07F 9/6658
USPC .............................. 546/22, 268.4; 514/89, 340
See application file for complete search history.

(56) References Cited

U.S. PATENT DOCUMENTS 7,148,219 B2 * 12/2006 Lou et al. ................... 514/235.5

FOREIGN PATENT DOCUMENTS

| | | |
|---|---|---|
| CN | 101560209 A | 10/2009 |
| CN | 101982468 A | 3/2011 |
| CN | 102153547 A | 8/2011 |
| CN | 102190656 A | 9/2011 |
| JP | 2006526647 A | 11/2006 |
| JP | 2011515487 A | 5/2011 |
| WO | WO-95/25106 | 9/1995 |
| WO | WO-02/06278 A1 | 1/2002 |
| WO | WO-2004/014392 A1 | 2/2004 |
| WO | WO-2005/054234 A2 | 6/2005 |
| WO | WO-2005/082899 A1 | 9/2005 |
| WO | WO-2011/097946 A1 | 8/2011 |

OTHER PUBLICATIONS

Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1996.*
National Committee for Clinical Laboratory Standards. 2006. Methods for Dilution Antimicrobial Susceptibility Tests for Bacteria That Grow Aerobically, Approved Standard—Seventh Edition M7-A7.

* cited by examiner

*Primary Examiner* — Patricia L Morris
(74) *Attorney, Agent, or Firm* — Cesari and McKenna LLP

(57) ABSTRACT

The present invention relates to a biaryl heterocycle substituted oxazolidinone antibacterials shown by general formula (I), a pharmaceutically acceptable salt thereof, an isomer or a prodrug thereof, wherein $R^1$, $R^2$, $R^3$, $R^4$, $R^5$, A and B are as defined in the description. The present invention further relates to a method for preparing the compound, a pharmaceutical composition and a pharmaceutical formulation comprising the compound, and a use of the compound in the manufacture of a medicament for the treatment and/or prevention of infectious diseases and a use for the treatment and/or prevention of infectious diseases.

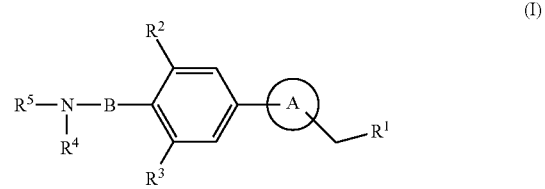

(I)

9 Claims, No Drawings

BIARYL HETEROCYCLE SUBSTITUTED OXAZOLIDINONE ANTIBACTERIAL AGENTS

CROSS REFERENCE TO RELATED APPLICATIONS

This application is the national stage entry under 35 USC 371 for PCT/CN2012/082318, filed on Sep. 28, 2012, which claims the benefit of the Sep. 29, 2011 priority date of Chinese Application No. 201110290839.X. The contents of the foregoing applications are incorporated herein by reference.

TECHNICAL FIELD

The present invention relates to the technical field of pharmaceuticals, and specifically related to a biaryl heterocycle substituted oxazolidinone antibacterials, a pharmaceutically acceptable salt thereof, an isomer thereof and a prodrug thereof, a method for preparing the compound, a pharmaceutical composition and a pharmaceutical formulation comprising the compound, a use of the compound for the manufacture of a medicament useful for the treatment and/or prevention of infectious diseases.

BACKGROUND

Oxazolidinones antibacterials are a novel class of completely chemically synthesized antibacterials with effects of inhibiting multidrug resistant Gram-positive bacteria following sulfonamides and fluoroquinolones.

Linezolid is the first oxazolidinones antibacterial in the market.

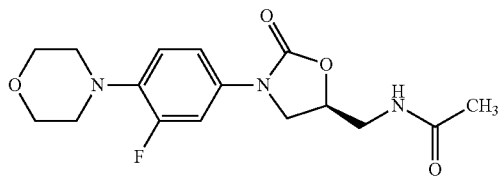 [SMILES: CC(=O)NC[C@H]1CN(c2ccc(N3CCOCC3)c(F)c2)C(=O)O1]

Linezolid has relatively strong effects of inhibiting Gram-positive bacteria and does not have cross resistance with other antibacterials. Linezolid has a unique mechanism of action and can inhibit the early phase of the synthesis of bacterioprotein. Linezolid is mainly used for treating infectious diseases induced by resistant Gram-positive bacteria, and can also be used for treating surgical infectious diseases.

CN201010508824.1 discloses TR-701, a pharmaceutical in phase III clinical trial from Trius Therapeutics Inc., which is metabolized in vivo to the active component TR-700, use for infectious diseases induced by Gram-positive bacteria, (TR-701)

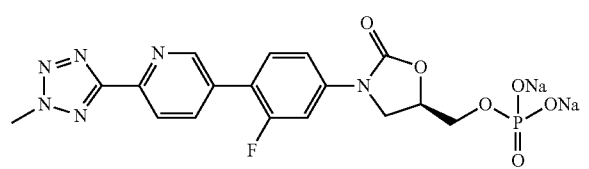

(TR-700)

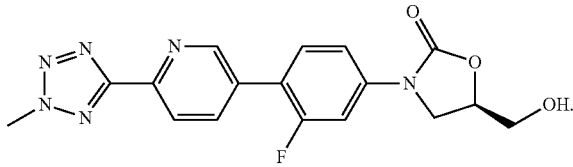

However, resistance of Gram-positive bacteria is getting more and more serious clinically. Oxazolidinones antibacterials have a very limited variety of pharmaceuticals for clinical use, currently only linezolid in the market, and cannot meet the clinical needs. In addition, the resistance to linezolid is getting more and more serious. Thus, there is an urgent need to expand varieties of clinically used oxazolidinones antibiotics, and develop antibacterials have highly effective against resistant Gram-positive bacteria.

SUMMARY

In order to meet clinical needs, the present invention provides a class of anti-infective compounds having a relatively high antibacterial activity. Specific embodiments are as follows:

A compound shown by general formula (I), a pharmaceutically acceptable salt thereof, an isomer thereof or a prodrug thereof:

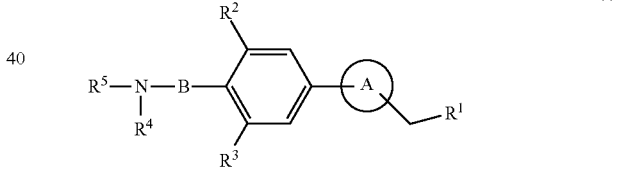

(I)

wherein, $R^1$ is selected from (1) —$OR^6$, (2) —$NR^6R^{6'}$, (3) —$COR^6$, (4) —$COOR^6$, (5) —$OCOR^6$, (6) —$CONR^6R^{6'}$, (7) —$NR^6COR^{6'}$, (8) —$OCONR^6R^{6'}$, (9) —$NR^6COOR^{6'}$, (10) —$NR^6CONR^{6'}R^6$, (11) —$CSR^6$, (12) —$CSOR^6$, (13) —$OCSR^6$, (14) —$CSNR^6R^{6'}$, (15) —$NR^6CSR^{6'}$, (16) —$OCSNR^6R^{6'}$, (17) —$NR^6CSOR^{6'}$, (18) —$NR^6CSNR^{6'}R^6$, (19) —$NR^6C(NR^6)NR^{6'}R^6$, (20) —$S(O)_pR^6$, (21) —$SO_2NR^6R^{6'}$, or (22) $R^6$, p is 0, 1 or 2, $R^6$, $R^{6'}$ are independently selected from: (1) hydrogen, (2) $C_{1-6}$ alkyl, (3) $C_{2-6}$ alkenyl, (4) $C_{2-6}$ alkynyl, (5) 3-14 membered cycloalkyl, (6) 6-14 membered aryl, (7) 3-14 membered heterocyclyl, containing one or more heteroatoms selected from N, S, O and/or $SO_2$, (8) —$COC_{1-6}$ alkyl, (9) —$COC_{2-6}$ alkenyl, or (10) —$COC_{2-6}$ alkynyl;

$R^2$, $R^3$ are independently selected from hydrogen, halogen or $C_{1-6}$ alkyl;

A is selected from

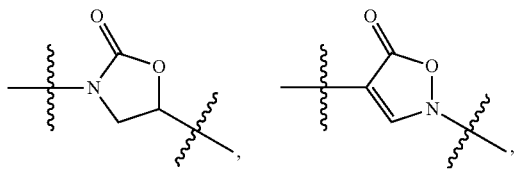

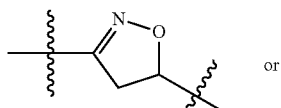 or

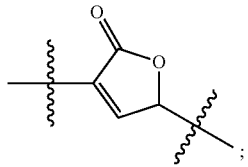 ;

B is selected from

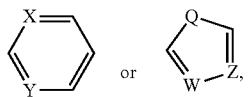

wherein X, Y, W, Z are each independently selected from C atom or N atom, and Q is independently selected from CH$_2$, NH, O atom or S atom;

R$^4$ is selected from: (1) hydrogen, (2) C$_{1-6}$ alkyl, (3) C$_{2-6}$ alkenyl, (4) C$_{2-6}$ alkynyl, (5) 3-14 membered cycloalkyl, (6) 6-14 membered aryl, (7) 3-14 membered heterocyclyl, containing one or more heteroatoms selected from N, S, O and/or SO$_2$, (8) —COC$_{1-6}$ alkyl, (9) —COC$_{2-6}$ alkenyl, or (10) —COC$_{2-6}$ alkynyl;

R$^5$ is selected from the following groups which are unsubstituted or substituted by 1-3R$^7$:

(1) 3-14 membered cycloalkyl,
(2) 6-14 membered aryl,
(3) 3-14 membered heterocyclyl, or
(4) 5-14 membered heteroaryl, R$^7$ is selected from halogen, carboxyl, hydroxyl, amino, cyano, nitro, C$_{1-4}$ alkyl, carboxyl C$_{1-4}$ alkyl, hydroxyl C$_{1-4}$ alkyl, amino C$_{1-4}$ alkyl, halo C$_{1-4}$ alkyl, C$_{1-4}$ alkoxyl, halo C$_{1-4}$ alkoxyl, C$_{1-4}$ alkoxyl C$_{1-4}$ alkyl, C$_{1-4}$ alkyl amino, di(C$_{1-4}$ alkyl)amino, di(C$_{1-4}$ alkyl)amino C$_{1-4}$ alkyl, C$_{1-4}$ alkyl carbonyl, C$_{1-4}$ alkyl carbonyloxy, C$_{1-4}$ alkoxyl carbonyl, carbamyl, carbamyl C$_{1-4}$ alkyl, C$_{1-4}$ alkyl carbamyl, di(C$_{1-4}$ alkyl)carbamyl, aminosulfonyl, aminosulfonyl C$_{1-4}$ alkyl, C$_{1-4}$ alkyl aminosulfonyl, di(C$_{1-4}$ alkyl)aminosulfonyl, C$_{1-4}$ alkyl sulfonylamino, C$_{1-4}$ alkyl sulfonyl, C$_{1-4}$ alkyl carbonylamino or guanidino.

Preferably, formula (I) has a structure shown by general formula (II) below:

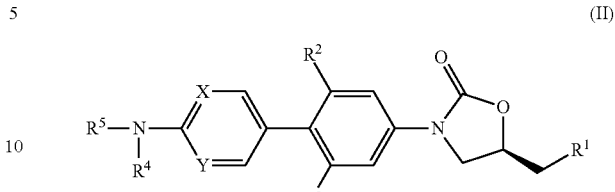

(II)

wherein, R$^1$, R$^2$, R$^3$, R$^4$, R$^5$, X and Y are as defined in general formula (I).

A compound as shown by general formula (II), a pharmaceutically acceptable salt thereof, an isomer thereof or a prodrug thereof, preferably is:

wherein,

R$^1$ is selected from —NHCOCH$_3$, —OH, —NH$_2$, —NHC$_{1-6}$ alkyl,

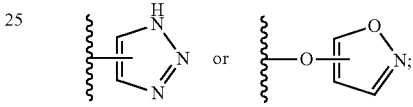

R$^2$, R$^3$ are independently selected from hydrogen or halogen;

X, Y are each independently selected from C atom or N atom;

R$^4$ is selected from: (1) hydrogen, (2) C$_{1-4}$ alkyl, (3) C$_{2-4}$ alkenyl, (4) C$_{2-4}$ alkynyl, (5) —C(O)C$_{1-4}$ alkyl, (6) —C(O)C$_{2-4}$ alkenyl, or (7) —C(O)C$_{2-4}$ alkynyl;

R$^5$ is selected from 5-14 membered heteroaryl, unsubstituted or substituted by 1-3 R$^7$, the 5-14 membered heteroaryl containing one or more heteroatoms selected from N, S, O and/or SO$_2$, R$^7$ is selected from halogen, carboxyl, hydroxyl, amino, cyano, nitro, C$_{1-4}$ alkyl, carboxyl C$_{1-4}$ alkyl, hydroxyl C$_{1-4}$ alkyl, amino C$_{1-4}$ alkyl, halo C$_{1-4}$ alkyl, C$_{1-4}$ alkoxyl, halo C$_{1-4}$ alkoxyl, C$_{1-4}$ alkoxyl C$_{1-4}$ alkyl, C$_{1-4}$ alkyl amino, di(C$_{1-4}$ alkyl)amino, di(C$_{1-4}$ alkyl)amino C$_{1-4}$ alkyl, C$_{1-4}$ alkyl carbonyl, C$_{1-4}$ alkyl carbonyloxy, C$_{1-4}$ alkoxyl carbonyl, carbamyl, carbamyl C$_{1-4}$ alkyl, C$_{1-4}$ alkyl carbamyl, di(C$_{1-4}$ alkyl)carbamyl, aminosulfonyl, aminosulfonyl C$_{1-4}$ alkyl, C$_{1-4}$ alkyl aminosulfonyl, di(C$_{1-4}$ alkyl)aminosulfonyl, C$_{1-4}$ alkyl sulfonylamino, C$_{1-4}$ alkyl sulfonyl, C$_{1-4}$ alkyl carbonylamino or guanidino.

A compound as shown by general formula (II), its pharmaceutically acceptable salt, isomer or prodrug thereof, preferably is:

wherein,

R$^1$ is selected from —NHCOCH$_3$ or —OH;

R$^2$, R$^3$ are independently selected from hydrogen or halogen;

R$^4$ is selected from hydrogen or C$_{1-4}$ alkyl;

X, Y are each independently selected from C atom or N atom;

R$^5$ is selected from 5-8 membered monoheteroaryl, unsubstituted or substituted by 1-3 R$^7$, the 5-8 membered monoheteroaryl containing one or more heteroatoms selected from N, S, O and/or SO$_2$, R$^7$ is selected from C$_{1-4}$ alkyl or halo C$_{1-4}$ alkyl.

A compound as shown by general formula (II), a pharmaceutically acceptable salt thereof, an isomer thereof or a prodrug thereof, preferably is:
wherein,
$R^1$ is selected from —NHCOCH$_3$ or —OH;
$R^2$ is hydrogen;
$R^3$ is fluoro;
$R^4$ is hydrogen;
X is C atom;
Y is N atom;
$R^5$ is selected from 5-6 membered monoheteroaryl, unsubstituted or substituted by 1-2 $R^7$, the 5-6 membered monoheteroaryl containing one or more heteroatoms selected from N, S or O,
$R^7$ is selected from $C_{1-4}$ alkyl or halo $C_{1-4}$ alkyl.

A compound shown by general formula (I), a pharmaceutically acceptable salt thereof, an isomer thereof or a prodrug thereof preferably is:
wherein,
$R^1$ is selected from —NHCOCH$_3$ or —OH;
$R^2$ is hydrogen;
$R^3$ is fluoro;
$R^4$ is hydrogen;
X is C atom;
Y is N atom;
$R^5$ is selected from pyrrolyl, furyl, imidazolyl, 1,2,4-triazolyl, 1,2,3-triazolyl, pyrazolyl, oxazolyl, isoxazolyl, 1,2,3-thiadiazolyl, 1,2,4-thiadiazolyl, 1,3,4-thiadiazolyl, 1,2,3-oxadiazolyl, 1,2,4-oxadiazolyl, 1,2,5-oxadiazolyl, pyridyl, pyrimidinyl, thiazolyl, isothiazolyl, 1,2,3,4-tetrazolyl, pyranyl or pyrazinyl, unsubstituted or substituted by 1-2 $R^7$,
$R^7$ is $C_{1-4}$ alkyl.

Preferably, formula (I) has a structure shown by general formula (III) below:

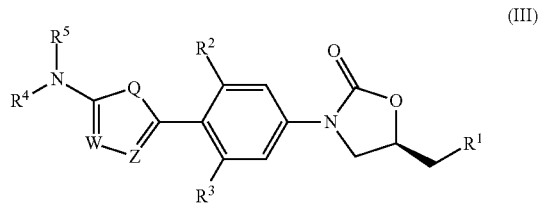

(III)

wherein, $R^1$, $R^2$, $R^3$, $R^4$, $R^5$, Q, W and Z are as defined in general formula (I).

A compound of general formula (III), a pharmaceutically acceptable salt thereof, an isomer thereof or a prodrug thereof, preferably is:
wherein,
$R^1$ is selected from —NHCOCH$_3$, —OH, —NH$_2$, —NHC$_{1-6}$ alkyl,

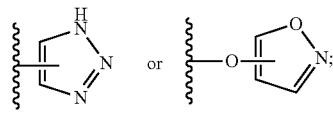

$R^2$, $R^3$ are independently selected from hydrogen or halogen;
W, Z are each independently selected from C atom or N atom, and Q is independently selected from CH$_2$, NH, O or S atom;

$R^4$ is selected from: (1) hydrogen, (2) $C_{1-4}$ alkyl, (3) $C_{2-4}$ alkenyl, (4) $C_{2-4}$ alkynyl, (5) —C(O)C$_{1-4}$ alkyl, (6) —C(O)C$_{2-4}$ alkenyl, or (7) —C(O)C$_{2-4}$ alkynyl;
$R^5$ is selected from 5-14 membered heteroaryl, unsubstituted or substituted by 1-3 $R^7$, the 5-14 membered heteroaryl containing one or more heteroatoms selected from N, S, O and/or SO$_2$,
$R^7$ is selected from halogen, carboxyl, hydroxyl, amino, cyano, nitro, $C_{1-4}$ alkyl, carboxyl $C_{1-4}$ alkyl, hydroxyl $C_{1-4}$ alkyl, amino $C_{1-4}$ alkyl, halo $C_{1-4}$ alkyl, $C_{1-4}$ alkoxyl, halo $C_{1-4}$ alkoxyl, $C_{1-4}$ alkoxyl $C_{1-4}$ alkyl, $C_{1-4}$ alkyl amino, di($C_{1-4}$ alkyl)amino, di($C_{1-4}$ alkyl)amino $C_{1-4}$ alkyl, $C_{1-4}$ alkyl carbonyl, $C_{1-4}$ alkyl carbonyloxy, $C_{1-4}$ alkoxyl carbonyl, carbamyl, carbamyl $C_{1-4}$ alkyl, $C_{1-4}$ alkyl carbamyl, di($C_{1-4}$ alkyl)carbamyl, aminosulfonyl, aminosulfonyl $C_{1-4}$ alkyl, $C_{1-4}$ alkyl aminosulfonyl, di($C_{1-4}$ alkyl)aminosulfonyl, $C_{1-4}$ alkyl sulfonylamino, $C_{1-4}$ alkyl sulfonyl, $C_{1-4}$ alkyl carbonylamino or guanidino.

A compound of general formula (III), a pharmaceutically acceptable salt thereof, an isomer thereof or a prodrug thereof, preferably is:
wherein,
$R^1$ is selected from —NHCOCH$_3$ or —OH;
$R^2$, $R^3$ are independently selected from hydrogen or halogen;
$R^4$ is selected from hydrogen or $C_{1-4}$ alkyl;
W, Z are each independently selected from C atom or N atom, and Q is independently selected from NH, O or S atom;
$R^5$ is selected from 5-8 membered monoheteroaryl, unsubstituted or substituted by 1-3 $R^7$, the 5-8 membered monoheteroaryl containing one or more heteroatoms selected from N, S, O and/or SO$_2$,
$R^7$ is selected from $C_{1-4}$ alkyl or halo $C_{1-4}$ alkyl.

Further preferably is:
wherein,
$R^1$ is selected from —NHCOCH$_3$ or —OH;
$R^2$ is hydrogen;
$R^3$ is fluoro;
$R^4$ is hydrogen;
W, Z are each independently selected from C atom or N atom, and Q is independently selected from O or S atom;
$R^5$ is selected from 5-6 membered monoheteroaryl, unsubstituted or substituted by 1-2 $R^7$, the 5-6 membered monoheteroaryl containing one or more heteroatoms selected from N, S or O,
$R^7$ is selected from $C_{1-4}$ alkyl or halo $C_{1-4}$ alkyl.

Further preferably is:
wherein,
$R^1$ is selected from —NHCOCH$_3$ or —OH;
$R^2$ is hydrogen;
$R^3$ is fluoro;
$R^4$ is hydrogen;
W is N atom, Z is C atom, and Q is S atom;
$R^5$ is selected from pyrrolyl, furyl, imidazolyl, 1,2,4-triazolyl, 1,2,3-triazolyl, pyrazolyl, oxazolyl, isoxazolyl, 1,2,3-thiadiazolyl, 1,2,4-thiadiazolyl, 1,3,4-thiadiazolyl, 1,2,3-oxadiazolyl, 1,2,4-oxadiazolyl, 1,2,5-oxadiazolyl, pyridyl, pyrimidinyl, thiazolyl, isothiazolyl, 1,2,3,4-tetrazolyl, pyranyl or pyrazinyl, unsubstituted or substituted by 1-2 $R^7$,
$R^7$ is $C_{1-4}$ alkyl.

Specific Embodiments
The "halogen" described by the present invention refers to fluoro atom, chloro atom, bromo atom, iodo atom and the like. Preferred are fluoro atom and chloro atom.
The "$C_{1-6}$ alkyl" described by the present invention refers to linear or branched alkyl containing 1-6 carbon atoms, such as methyl, ethyl, n-propyl, iso-propyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like. Preferred are $C_{1-4}$ alkyl. The "$C_{1-4}$ alkyl" described by the present invention refers to the above examples containing 1-4 carbon atoms.

The "$C_{2-6}$ alkenyl" described by the present invention refers to linear or branched or cyclic alkenyl with 2-6 carbon atoms and containing a double bond, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 2,4-pentadienyl, 1,4-hexadienyl, 2,4-hexadienyl, cyclopentenyl, 1,3-cyclopentadienyl, cyclohexenyl and 1,4-cyclohexadienyl and the like. The double bond can be optionally cis and trans.

The "$C_{2-6}$ alkynyl" described by the present invention refers to linear or branched alkynyl with 2-6 carbon atoms containing a triple bond, such as ethynyl, 1-propynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl and the like.

The "$C_{1-6}$ alkoxyl", "$C_{1-6}$ alkyl amino", "di($C_{1-6}$ alkyl) amino", "$C_{1-6}$ alkyl carbonyloxy", "$C_{1-6}$ alkoxyl carbonyl", "$C_{1-6}$ alkyl carbonyl", "$C_{1-6}$ alkyl sulfonyl", "$C_{1-6}$ alkyl sulfonylamino", "$C_{1-6}$ alkyl carbonylamino", "$C_{1-6}$ alkyl carbamyl", "di($C_{1-6}$ alkyl)carbamyl", "$C_{1-6}$ alkyl aminosulfonyl", "di($C_{1-6}$ alkyl)aminosulfonyl" described by the present invention respectively refer to "$C_{1-6}$ alkyl-O—" group, "$C_{1-6}$ alkyl-NH—" group, "($C_{1-6}$ alkyl)$_2$N—" group, "$C_{1-6}$ alkyl-C(O)—O—" group, "$C_{1-6}$ alkyl-O—C(O)—" group, "$C_{1-6}$ alkyl-C(O)—" group, "$C_{1-6}$ alkyl-SO$_2$—" group, "$C_{1-6}$ alkyl-SO$_2$—NH—" group, "$C_{1-6}$ alkyl-C(O)—NH—" group, "$C_{1-6}$ alkyl-NH—C(O)—" group, "($C_{1-6}$ alkyl)$_2$N—C(O)—" group, "$C_{1-6}$ alkyl-NH—SO$_2$—" group, "($C_{1-6}$ alkyl)$_2$N—SO$_2$—" group, wherein the "$C_{1-6}$ alkyl" is as defined above.

The "$C_{1-4}$ alkoxyl", "$C_{1-4}$ alkyl amino", "di($C_{1-4}$ alkyl) amino", "$C_{1-4}$ alkyl carbonyloxy", "$C_{1-4}$ alkoxyl carbonyl", "$C_{1-4}$ alkyl carbonyl", "$C_{1-4}$ alkyl sulfonyl", "$C_{1-4}$ alkyl sulfonylamino", "$C_{1-4}$ alkyl carbonylamino", "$C_{1-4}$ alkyl carbamyl", "di($C_{1-4}$ alkyl)carbamyl", "$C_{1-4}$ alkyl aminosulfonyl", "di($C_{1-4}$ alkyl)aminosulfonyl" described by the present invention respectively refer to "$C_{1-4}$ alkyl-O—" group, "$C_{1-4}$ alkyl-NH—" group, "($C_{1-4}$ alkyl)$_2$N—" group, "$C_{1-4}$ alkyl-C(O)—O—" group, "$C_{1-4}$ alkyl-O—C(O)—" group, "$C_{1-4}$ alkyl-C(O)—" group, "$C_{1-4}$ alkyl-SO$_2$—" group, "$C_{1-4}$ alkyl-SO$_2$—NH—" group, "$C_{1-4}$ alkyl-C(O)—NH—" group, "$C_{1-4}$ alkyl-NH—C(O)—" group, "($C_{1-4}$ alkyl)$_2$N—C(O)—" group, "$C_{1-4}$ alkyl-NH—SO$_2$—" group, "($C_{1-4}$ alkyl)$_2$N—SO$_2$—" group, wherein the "$C_{1-4}$ alkyl" is as defined above.

The "hydroxyl $C_{1-6}$ alkyl", "carboxyl $C_{1-6}$ alkyl", "amino $C_{1-6}$ alkyl", "aminosulfonyl $C_{1-6}$ alkyl", "di($C_{1-6}$ alkyl)amino $C_{1-6}$ alkyl", "$C_{1-6}$ alkoxyl $C_{1-6}$ alkyl", "carbamyl $C_{1-6}$ alkyl" described by the present invention respectively refer to a group formed by substituting $C_{1-6}$ alkyl with one or more hydroxyl, carboxyl, amino, aminosulfonyl, di($C_{1-6}$ alkyl) amino, $C_{1-6}$ alkoxyl, carbamyl, wherein the "$C_{1-6}$ alkyl" is as defined above.

The "hydroxyl $C_{1-4}$ alkyl", "carboxyl $C_{1-4}$ alkyl", "amino $C_{1-4}$ alkyl", "aminosulfonyl $C_{1-4}$ alkyl", "di($C_{1-4}$ alkyl)amino $C_{1-4}$ alkyl"; "$C_{1-4}$ alkoxyl $C_{1-4}$ alkyl", "carbamyl $C_{1-4}$ alkyl" described by the present invention respectively refer to a group formed by substituting $C_{1-4}$ alkyl with one or more hydroxyl, carboxyl, amino, aminosulfonyl, di($C_{1-4}$ alkyl) amino, $C_{1-4}$ alkoxyl, carbamyl, wherein the "$C_{1-4}$ alkyl" is as defined above.

The "halo $C_{1-6}$ alkyl" described by the present invention refers to a group formed by substituting "$C_{1-6}$ alkyl" with one or more "halogen" atoms, and the "halo $C_{1-4}$ alkyl" refers to a group formed by substituting "$C_{1-4}$ alkyl" with one or more "halogen" atoms, wherein the "halogen" and the "$C_{1-6}$ alkyl", the "$C_{1-4}$ alkyl" are as defined above.

The "halo $C_{1-6}$ alkoxyl" described by the present invention refers to a group formed by substituting "$C_{1-6}$ alkoxyl" with one or more "halogen" atoms, and "halo $C_{1-4}$ alkoxyl" refers to a group formed by substituting "$C_{1-4}$ alkoxyl" with to one or more "halogen" atoms, wherein the "halogen", "$C_{1-6}$ alkoxyl", "$C_{1-4}$ alkoxyl" are as defined above.

The "3-14 membered cycloalkyl" described by the present invention refers to a group derived by removing a hydrogen atom from a cyclic alkane portion of 3-14 carbon atoms, including 3-8 membered monocycloalkyl, 6-14 membered fused cycloalkyl, preferably 3-8 membered monocycloalkyl, 3-6 membered monocycloalkyl and 5-6 membered monocycloalkyl. The "3-8 membered monocycloalkyl", "3-6 membered monocycloalkyl", and "5-6 membered cycloalkyl" are specific examples of the examples below containing 3-8, 3-6, and 5-6 carbon atoms, respectively.

Examples of the 3-8 membered monocycloalkyl include but are not limited to: cyclopropyl, cyclobutyl, cyclopentyl, cyclohexyl, cycloheptyl, cyclooctyl, methylcyclopropyl, dimethylcyclopropyl, methyl cyclobutyl, dimethylcyclobutyl, methylcyclopentyl, dimethylcyclopentyl, methylcyclohexyl, dimethylcyclohexyl and the like.

The 6-14 membered fused cycloalkyl refers to 6-14 membered cyclic group formed by two or more cyclic structures sharing two adjacent carbon atoms, preferably 6-12 membered fused cycloalkyl, 6-10 membered fused cycloalkyl, Examples thereof include but are not limited to: bicyclo[3.1.0]hexyl, bicyclo[4.1.0]heptyl, bicyclo[2.2.0]hexyl, bicyclo[3.2.0]heptyl, bicyclo[4.2.0]octyl, octahydrocyclopentadienyl, octahydro-1H-indenyl, decahydronaphthyl, tetradecahydrophenanthryl and the like.

The 7-12 membered bridged ring group refers to a structure containing 7-12 carbon atoms or/and heteroatoms formed by any two rings sharing two non-adjacent atoms, the heteroatoms being selected from N, S, O, CO, SO and/or SO$_2$ and the like, in which included are, for example, "7-10 membered bridged ring group", "7-9 membered bridged ring group", "7-8 membered bridged ring group" and the like. Examples thereof include but are not limited to, for example:

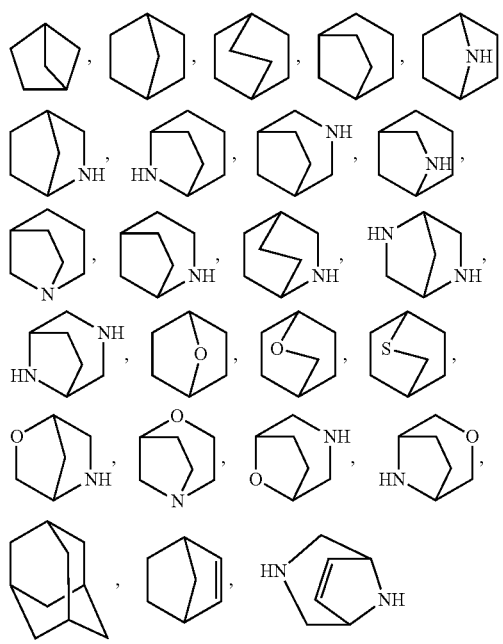

and the like.

The 7-12 membered spiro ring group refers to a structure containing 7-12 carbon atoms or/and heteroatoms formed by at least two rings sharing an atom, the heteroatoms being selected from N, S, O, CO, SO and/or SO$_2$ and the like, in which included are, for example, "7-10 membered spiro ring group", "7-9 membered spiro ring group", "7-8 membered spiro ring group" and the like. Examples thereof include but are not limited to, for example:

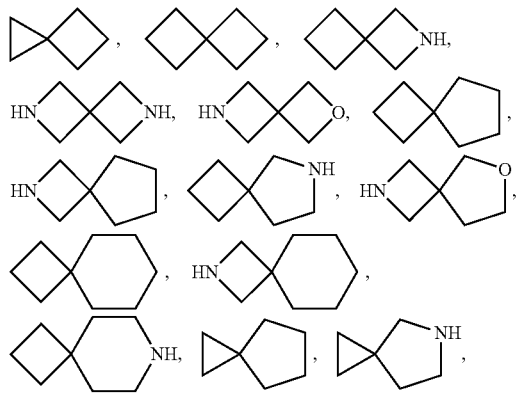

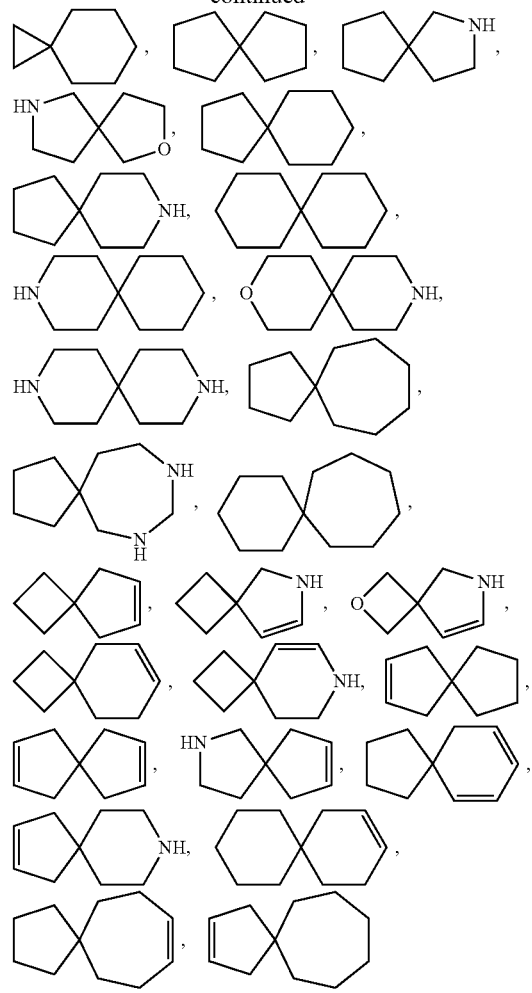

and the like.

The "6-14 membered aryl" described by the present invention refers to a cyclic aromatic group having 6-14 carbon atoms, including 6-8 membered monocyclic aryl and 8-14 membered fused aryl. The 6-8 membered monocyclic aryl includes phenyl, cyclooctatetraenyl and the like. The 8-14 membered fused aryl refers to a cyclic group formed by two or more cyclic structures sharing two adjacent carbon atoms with each other, including naphthyl, anthryl and phenanthryl and the like, further including 8-14 membered partially saturated fused aryl, for example, benzo 3-8 membered monocyclic cycloalkyl. Specific examples are, for example, 2,3-dihydro-1H-indenyl, 1H-indenyl, 1,2,3,4-tetrahydronaphthyl, 1,4-dihydronaphthyl and the like. Preferred are 6-10 membered aryl, and further preferred are phenyl or benzo 3-8 membered monocyclic cycloalkyl.

The "5-14 membered heteroaryl", the ring atoms, also include one or more heteroatoms other than carbon atoms, the "heteroatoms" being selected from N, S, O, CO, SO and/or SO$_2$ and the like. The heteroaryl can be bonded via carbon or hetero atoms in the ring. Included 5-8 membered monoheteroaryl and 8-14 membered fused heteroaryl.

The 5-8 membered monoheteroaryl, preferably 5-6 membered monoheteroaryl, include but are not limited to pyrrolyl, imidazolyl, pyrazolyl, 1,2,3-triazolyl, 1,2,4-triazolyl, pyridyl, furyl, thienyl, oxazolyl, isoxazolyl, thiazolyl, isothiazolyl, 1,2,3-thiadiazolyl, 1,2,4-thiadiazolyl, 1,3,4- thiadiazolyl, 1,2,3-oxadiazolyl, 1,2,4-oxadiazolyl, 1,2,5-oxadiazolyl, 1,2,3-triazinyl, 1,2,4-triazinyl, tetrazolyl, oxatriazolyl, 2H-1,2-oxazinyl, 4H-1,2-oxazinyl, 6H-1,2-oxazinyl, 2H-1,3-oxazinyl, 4H-1,3-oxazinyl, 6H-1,3-oxazinyl, 2H-1,4-oxazinyl, 4H-1,4-oxazinyl, isoxazinyl, pyridazinyl, pyrimidinyl and pyrazinyl and the like;

The 8-14 membered fused heteroaryl include but are not limited to benzofuryl, isobenzofuryl, benzothienyl, indolyl, isoindolyl, quinolinyl, isoquinolinyl, indolizinyl, indazolyl, phthalazinyl, quinoxalinyl, quinazolinyl, benzodiazinyl, benzoisoxazolyl, benzoxazinyl, benzimidazolyl, pyridopyridyl, pyrazolo[3,4-b]pyridyl, purinyl, acridinyl and xanthenyl and the like.

The "3-14 membered heterocyclyl" described by the present invention refers to a 3-14 membered cyclic group containing one or more heteroatoms, the "heteroatoms" being selected from N, S, O, CO, SO and/or $SO_2$ and the like. Included 3-8 membered monoheterocyclyl and 6-14 membered fused heterocyclyl.

The 3-8 membered monoheterocyclyl refers to a monocyclic heterocyclyl containing 3-8 ring atoms (wherein contains at least one heteroatom), preferably 5-7 membered monoheterocyclyl. Specific examples include but are not limited to 2,5-dihydrothienyl, 4,5-dihydro pyrazolyl, 3,4-dihydro-2H-pyranyl, 5,6-dihydro-4H-1,3-oxazinyl, azacyclopropyl, azacyclobutyl, thiacyclobutyl, tetrahydrofuryl, tetrahydropyrrolyl, imidazolidinyl, pyrazolidinyl, tetrahydrofuryl, 1,4-dioxacyclohexyl, 1,3-dioxacyclohexyl, 1,3-dithiacyclohexyl, morpholinyl, piperazinyl and the like.

The 6-14 membered fused heterocyclyl refers to a fused ring structure containing 6-14 ring atoms (wherein containing at least one heteroatom) formed by two or more cyclic structures connected by sharing two adjacent atoms with each other, preferably 6-10 membered fused heterocyclyl, such as a structure formed by benzo 3-8 membered monoheterocyclyl, a structure formed by 3-8 membered monoheterocyclyl fused with 3-8 membered monoheterocyclyl. Specific examples include but are not limited to: 1,3-dihydrobenzofuryl, benzo[d][1.3]dioxolyl, isoindolinyl, chromanyl, 1,2,3,4-tetrahydropyrrolo[3,4-c]pyrrole,

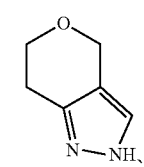

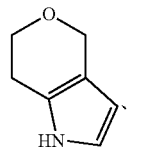

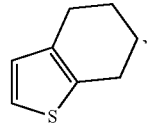

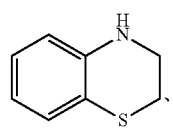

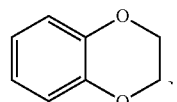

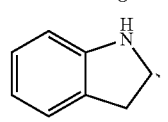

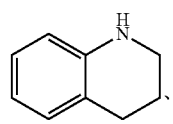

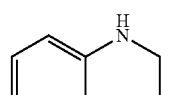

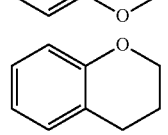

and the like.

The "1-3" described by the present invention refers to 1, 2 or 3.

The "3-8 membered" described by the present invention refers to 3, 4, 5, 6, 7 or 8 membered, preferably 5-8 membered, further preferably 5-7 membered, even further preferably 5-6 membered.

TABLE 1

Compounds of the present invention

| Compounds | Chemical Names | Structural Formula |
| --- | --- | --- |
| 1 | (R)-3-(3-fluoro-4-(6-((2-methyl-2H-tetrazol-5-yl)amino)pyridin-3-yl)phenyl)-5-(hydroxylmethyl)oxazolidin-2-one | |

TABLE 1-continued

Compounds of the present invention

| Compounds | Chemical Names |
|---|---|
| 2 | (R)-(3-(3-fluoro-4-(6-((2-methyl-2H-tetrazol-5-yl)amino)pyridin-3-yl)phenyl)-2-oxooxazolidin-5-yl)methyl phosphate disodium salt |
| 3 | (S)-N-((3-(3-fluoro-4-(6-((2-methyl-2H-tetrazol-5-yl)amino)pyridin-3-yl)phenyl)-2-oxooxazolidin-5-yl)methyl)acetamide |
| 4 | (R)-3-(3-fluoro-4-(6-((1-methyl-1H-tetrazol-5-yl)amino)pyridin-3-yl)phenyl)-5-(hydroxylmethyl)oxazolidin-2-one |
| 5 | (R)-(3-(3-fluoro-4-(6-((1-methyl-1H-tetrazol-5-yl)amino)pyridin-3-yl)phenyl)-2-oxooxazolidin-5-yl)methyl phosphate disodium salt |
| 6 | (R)-3-(3-fluoro-4-(6-(methyl(1-methyl-1H-tetrazol-5-yl)amino)pyridin-3-yl)phenyl)-5-(hydroxylmethyl)oxazolidin-2-one |
| 7 | (R)-(3-(3-fluoro-4-(6-(methyl(1-methyl-1H-tetrazol-5-yl)amino)pyridin-3-yl)phenyl)-2-oxooxazolidin-5-yl)methyl phosphate disodium salt |
| 8 | (R)-3-(3-fluoro-4-(6-(methyl(2-methyl-2H-tetrazol-5-yl)amino)pyridin-3-yl)phenyl)-5-(hydroxylmethyl)oxazolidin-2-one |

TABLE 1-continued

Compounds of the present invention

| Compounds | Chemical Names | Structural Formula |
|---|---|---|
| 9 | (R)-(3-(3-fluoro-4-(6-(methyl(2-methyl-2H-tetrazol-5-yl)amino)pyridin-3-yl)phenyl)-2-oxooxazolidin-5-yl)methyl phosphate disodium salt | |
| 10 | (R)-3-(3-fluoro-4-(6-((1-methyl-1H-pyrazol-3-yl)amino)pyridin-3-yl)phenyl)-5-(hydroxylmethyl)oxazolidin-2-one | |
| 11 | (R)-3-(3-fluoro-4-(6-((1-methyl-1H-1,2,3-triazol-4-yl)amino)pyridin-3-yl)phenyl)-5-(hydroxylmethyl)oxazolidin-2-one | |
| 11a | (R)-3-(3-fluoro-4-(6-((1-methyl-1H-1,2,3-triazol-5-yl)amino)pyridin-3-yl)phenyl)-5-(hydroxylmethyl)oxazolidin-2-one | |
| 12 | (R)-3-(3-fluoro-4-(6-((2-methyl-2H-1,2,3-triazol-4-yl)amino)pyridin-3-yl)phenyl)-5-(hydroxylmethyl)oxazolidin-2-one | |
| 13 | (R)-3-(4-(6-((2H-1,2,3-triazol-4-yl)amino)pyridin-3-yl)-3-fluorophenyl)-5-(hydroxylmethyl)oxazolidin-2-one | |
| 13a | 3-(4-(6-((1H-1,2,3-triazol-4-yl)amino)pyridin-3-yl)-3-fluorophenyl)-5-(hydroxylmethyl)oxazolidin-2-one | |

TABLE 1-continued

Compounds of the present invention

| Compounds | Chemical Names | Structural Formula |
|---|---|---|
| 14 | (R)-3-(3-fluoro-4-(2-((2-methyl-2H-tetrazol-5-yl)amino)thiazol-5-yl)phenyl)-5-(hydroxylmethyl)oxazolidin-2-one | |
| 15 | (R)-(3-(3-fluoro-4-(6-((1-methyl-1H-pyrazol-3-yl)amino)pyridin-3-yl)phenyl)-2-oxooxazolidin-5-yl)methyl phosphate disodium salt | |
| 16 | (R)-(3-(3-fluoro-4-(6-((1-methyl-1H-1,2,3-triazol-4-yl)amino)pyridin-3-yl)phenyl)-2-oxooxazolidin-5-yl)methyl phosphate disodium salt | |
| 17 | (R)-(3-(3-fluoro-4-(6-((2-methyl-2H-1,2,3-triazol-4-yl)amino)pyridin-3-yl)phenyl)-2-oxooxazolidin-5-yl)methyl phosphate disodium salt | |
| 18 | (R)-(3-(4-(6-((2H-1,2,3-triazol-4-yl)amino)pyridin-3-yl)-3-fluorophenyl)-2-oxooxazolidin-5-yl)methyl phosphate disodium salt | |
| 19 | (R)-(3-(3-fluoro-4-(2-((2-methyl-2H-tetrazol-5-yl)amino)thiazol-5-yl)phenyl)-2-oxooxazolidin-5-yl)methyl phosphate disodium salt | |

The present invention also provides methods for preparing the above compounds, which are not limited to the methods below:

Reaction Equations:

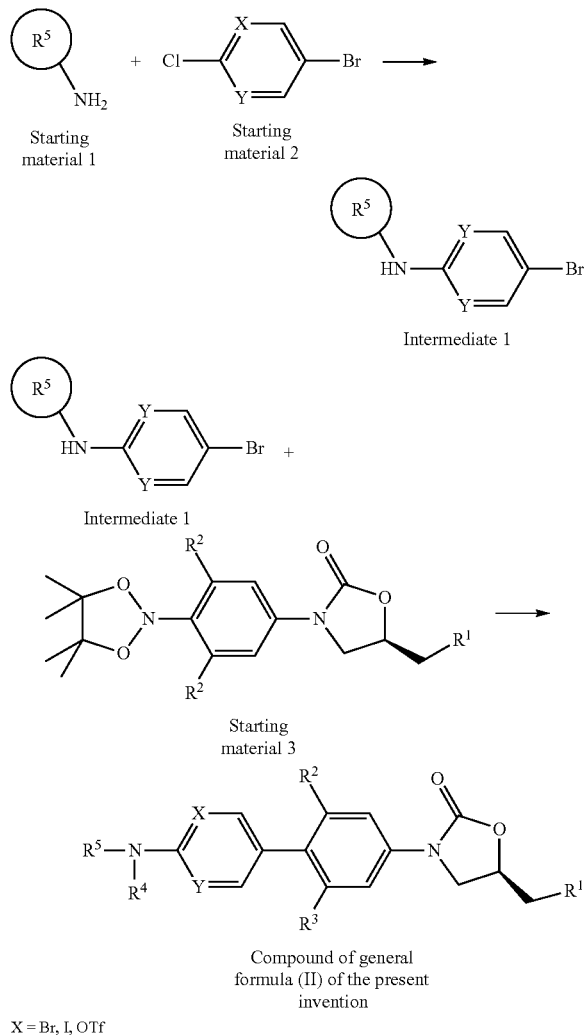

X = Br, I, OTf

Reaction Steps:

Step 1. Preparation of Intermediate 1

The starting material 1, the starting material 2, an inorganic base (such as potassium tert-butylate, cesium carbonate, potassium carbonate and the like) and a palladium catalyst (such as $Pd(dppf)Cl_2$, $Pd_2(dba)_3$, $Pd(PPh_3)_4$, $Pd(PPh_3)_2Cl_2$ and the like), BINAP were dissolved in toluene, heated under reflux and reacted overnight. Water was added, and the reaction was extracted with ethyl acetate. The organic phase was dried, concentrated, and the solid was separated by a silica gel column to obtain the intermediate 1.

Step 2. Preparation of Compound of General Formula (II) of the Present Invention The intermediate 1, the starting material 3, an inorganic base (such as cesium carbonate, potassium carbonate and the like) and a palladium catalyst (such as $Pd(dppf)Cl_2$, $Pd(PPh_3)_4$, $Pd(PPh_3)_2Cl_2$ and the like) were dissolved in dioxane and water, heated under reflux and reacted until the starting materials were consumed. The solvent was evaporated to dryness, and the solid was separated and purified by a silica gel column to obtain compound of general formula (II) of the present invention.

$R^1$, $R^2$, $R^3$, $R^4$, $R^5$, $R^6$, X or Y in the above reaction equations are as defined above.

The compound of general formula (III) of the present invention can be prepared according to the process for compound of general formula (II).

"A pharmaceutically acceptable salt" of the compound of the present invention refers to a base addition salt or an acid addition salt formed by the compound of the present invention with a pharmaceutically acceptable, non-toxic base or acid, including organic acid salts, inorganic acid salts, organic base salts, and inorganic base salts. Organic acid salts include formate, acetate, propionate, benzene sulfonate, benzoate, p-toluene sulfonate, 2,3-dihydroxybutanedioate, camphor sulfonate, citrate, methane sulfonate, ethane sulfonate, propane sulfonate, fumarate, glyconate, glutamate, hydroxyethyl sulfonate, lactate, maleate, malate, mandelate, mucate, bishydroxylnaphthoate, pantothenate, succinate, tartrate and the like. Specifically preferable are benzoate, benzene sulfonate, p-toluene sulfonate, methane sulfonate, citrate, maleate, fumarate, tartrate. Inorganic acid salts include hydrochloride, hydrobromide, hydroiodide, sulfate, phosphate, nitrate and the like. Specifically preferable are hydrochloride, hydrobromide, sulfate, phosphate. Organic base salts include amine salts, including salts formed with primary, secondary and tertiary amines, cyclic amine and basic ion exchange resin, which can be selected from salts formed with the following organic bases: for example, arginine, betaine, caffeine, choline, N,N'-dibenzylethylenediamine, diethylamine, 2-diethyl amino ethanol, 2-dimethylaminoethanol, ethanolamine, ethylenediamine, N-ethyl-morpholine, N-ethylpiperidine, meglumine, aminoglucose, histidine, hydrabamine, iso-propylamine, lysine, methylglucosamine, morpholine, piperazine, piperidine, procaine, purine, theobromine, triethylamine, trimethylamine, tripropylamine and tromethamine and the like. Inorganic base salts include salts formed with ammonia, alkali metals, and alkali earth metals, for example, ammonium salt and lithium salt, sodium salt, potassium salt, calcium salt, magnesium salt, zinc salt, barium salt, aluminum salt, ferric salt, cupric salt, ferrous salt, manganese salt, manganous salt. Specifically preferable are ammonium salt and sodium salt, potassium salt, calcium salt, magnesium salt. The compound of formula (I) of the present invention forms phosphate with phosphoric acid, and further forms phosphate metal salt of compound of formula (I) with metal salt, for example, phosphate disodium salt.

"A prodrug" of the compound of the present invention refers to a compound which can be converted to any compounds of formula (I) or converted to a pharmaceutically acceptable salts of the compounds of formula (I) under physiological condition or via dissolution in solvent (referred as an active drug). When being administered to a patient, the prodrug can be inactive, but it is converted in vivo to an active drug. When hydroxyl is present in the compound of formula (I) of the present invention, an ester-type prodrug can be formed with amino acid, phosphoric acid and the like, and the prodrug is stable in water or acid solution, but dissociates to a free active compound under the action of esterase or phosphatase in blood. The prodrug of the compound of formula (I) of the present invention has better solubility than the active drug, is more accessible to be absorbed by an animal or human, and can be converted to an active drug compound better in the blood to exert antibacterial activity.

"Isomers" of the compound of the present invention refers to compounds having the same chemical formula but differ in structure, including conformational isomer (structural isomer) and stereoisomer (configuration isomer) and the like. "Stereoisomer" refers to that when the compound of the present invention contains one or more asymmetric centers, it can be a racemate and a racemic mixture, a single enantiomer, a diastereomeric mixture and a single diastereomer. The compound of the present invention has asymmetric centers, which independently generate two optical isomers, respectively. The scope of the present invention encompasses all possible optical isomers and diastereomeric mixture and pure or partially pure compounds. If the compound described by the present invention contains an olefinic double bond, the present invention encompasses cis-isomer and trans-isomer, unless specified otherwise.

The compound described by the present invention can also present as tautomers, which have different positions of attaching to hydrogen by displacement of one or more double bonds. Each tautomer and mixtures thereof are encompassed within the scope of the present invention.

For example, tautomerism occurs in the compound represented by formula (I) of the present invention and intermediates during preparation thereof, when $R^5$ representing

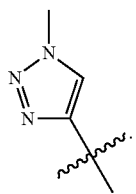 [SMILES: *c1cn(C)nn1]

If one of the tautomers is prepared, other tautomers are prepared as well. All the compounds of the present invention and intermediates during preparation involving the above circumstance are regarded equal, and are encompassed within the scope of the present invention.

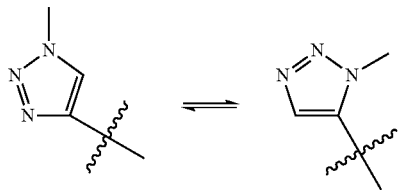

The present invention further provides a pharmaceutical composition comprising the above mentioned compound of general formula (I) of the present invention or a pharmaceutically acceptable salt thereof, an isomer thereof or a prodrug thereof, and one or more pharmaceutically acceptable carriers and/or diluents. The composition can be made into any clinically or pharmaceutically acceptable dosage form, preferably oral formulation and injection.

The compounds of the present invention or a pharmaceutically acceptable salt thereof or an isomer thereof can be administered to a mammal, for example human, orally, parenterally (intravenously, intramuscularly, subcutaneously or rectally), topically and the like. The compound of the present invention is used in an amount of about 0.1-100 mg/kg of body weight/day, for example, 3-50 mg/kg of body weight/day.

When being used for parenteral administration, the compound of the present invention or a pharmaceutically acceptable salt thereof or an isomer thereof can be formulated into an injection preparation, including sterile solution, emulsion, dispersion or suspension formulations, and sterile powder or concentrated solution for injection formulated or diluted into solution, dispersion or suspension before use, for intramuscular injection, intravenous injection, subcutaneous injection and the like.

The injection preparation can be produced by conventional procedures in the pharmaceutical field, by using aqueous solvents or nonaqueous solvents. The most commonly used aqueous solvent is water for injection, and 0.9% sodium chloride solution or other suitable aqueous solutions can also be used; commonly used nonaqueous solvents are vegetable oil, for example soybean oil for injection, as well as aqueous solutions of ethanol, propylene glycol, polyethylene glycol and the like. The injection preparation can be formulated without adding additives, or suitable additives, such as osmotic modifier, pH modifier, solubilizer, filler, antioxidant, bacteriostat, emulsifier, suspending agent and the like, can be added according to the property of the drug. Commonly used osmotic modifiers include sodium chloride, glucose, potassium chloride, magnesium chloride, calcium chloride, sorbitol and the like, preferably sodium chloride or glucose. Commonly used pH modifiers include acetic acid-sodium acetate, lactic acid, citric acid-sodium citrate, sodium bicarbonate-sodium carbonate and the like. Commonly used solubilizers include Polysorbate 80, propylene glycol, lecithin, polyoxyethylenated castor oil and the like. Commonly used fillers include lactose, mannitol, sorbitol, dextran and the like. Commonly used antioxidants include sodium sulfite, sodium bisulfite, sodium metabisulfite and the like. Commonly used bacteriostats are phenol, cresol, trichloro-tert-butanol and the like.

The pharmaceutical composition can also be formulated to dosage forms for rectal or topical administration, including suppository, ointment, cream, patch, powder, spray, inhalant and the like by conventional methods.

When being used for oral administration, the compound of the present invention or a pharmaceutically acceptable salt thereof or an isomer thereof can be formulated by conventional methods into conventional solid formulations, such as tablet, capsule, pill, granule and the like; and can be formulated into oral liquid formulations, such as oral solution, oral suspension, syrup and the like. Tablets are predominantly oral compressed tablets, and include buccal tablet, sublingual tablet, buccal patch, chewable tablet, dispersible tablet, soluble tablet, effervescent tablet, sustained release tablet, controlled release tablet and enteric coated tablet and the like. Based on the solubility and release properties thereof, capsules can be divided into hard capsule, soft capsule, sustained release capsule, controlled release capsule and enteric coated capsule and the like. Pills include dripping pill, rotula, parvule and the like. Granules can be divided into soluble granule, suspensible granule, effervescent granule, enteric coated granule, sustained release granule and controlled release granule and the like.

In the preparation of oral formulation, suitable filler, binder, disintegrant, lubricant and the like can be added. Commonly used fillers include starch, powdered sugar, calcium phosphate, calcium sulfate dihydrate, dextrin, microcrystalline cellulose, lactose, pregelatinized starch, mannitol and the like. Commonly used binders include sodium carboxymethyl cellulose, PVP-K30, sodium hydroxypropyl cellulose, starch slurry, methyl cellulose, ethyl cellulose, hydroxypropyl methylcellulose, gelatinized starch and the like. Commonly used disintegrants include dry starch, crospovidone, crosslinked sodium carboxymethyl cellulose, sodium carboxymethyl starch, low-substituted hydroxypropyl cellulose and the like. Commonly used lubricants include magnesium stearate, talc powder, sodium dodecylsulfate, micronized silica gel and the like.

Test Compounds:
Compounds 1, 3, 4, 6, 8, 11 of the present invention, prepared according to the process in each of the examples.
Control pharmaceutical: linezolid.
Test Method:
standard agar dilution method, reference was made to National Committee for Clinical Laboratory Standards. 2006. Methods for Dilution Antimicrobial Susceptibility Tests for Bacteria That Grow Aerobically, Approved Standard—Seventh Edition M7-A7.
Test Results and Conclusion:

TABLE 1

The antibacterial activity of the compounds of the present invention (ug/mL)

| Test compound | MRSA (ug/mL) | MRSE (ug/mL) | MSSA (ug/mL) | MSSE (ug/mL) | Enterococcus faecalis (ug/mL) | Enterococcus faecium (ug/mL) | Streptococcus pneumoniae (ug/mL) |
|---|---|---|---|---|---|---|---|
| linezolid | 4 | 2 | 2 | 2 | 4 | 4 | 2 |
| Compound 1 | 1 | 0.5 | 1 | 0.5 | 1 | 1 | 0.5 |
| Compound 3 | 1 | 0.25 | 0.5 | 0.25 | 0.25 | 0.25 | 0.25 |
| Compound 4 | 0.25 | 0.125 | 0.25 | 0.125 | 0.25 | 0.25 | 1 |
| Compound 6 | 0.5 | 0.5 | 0.5 | 0.5 | 1 | 1 | 0.5 |
| Compound 8 | 1 | 0.5 | 1 | 0.5 | 1 | 1 | 0.5 |
| Compound 11 | 1 | 1 | 1 | 0.5 | 2 | 2 | 1 |

In another aspect, the present invention further provides a use of the compound of general formula (I) of the present invention or a pharmaceutically acceptable salt thereof or an isomer thereof for the manufacture of a medicament for the treatment and/or prevention of infectious diseases.

In yet another aspect, the present invention further provides a method for treating and/or preventing infectious diseases, which comprises administering the compound of general formula (I) of the present invention or a pharmaceutically acceptable salt thereof or an isomer thereof to a mammal, for example human in need of the treatment or prevention.

Tests prove that the compounds of the present invention have good antibacterial activity, and can be used for the treatment and/or prevention of various infectious diseases.

The oxazolidinones antibacterials of the present invention have good antibacterial activity against Gram-positive bacteria, as well as good antibacterial activity against drug resistant Gram-positive bacteria, and can be used for the treatment and/or prevention of various diseases induced by Gram-positive bacteria.

The beneficial effects of the compounds of the present invention are further illustrated by antibacterial activity assays. However, it should not be interpreted as the compounds of the present invention only have, the following beneficial effects.

Example 1

The In Vitro Antibacterial Activity of the Compounds of the Present Invention

Strains for test: methicillin-resistant *Staphylococcus aureus* (MRSA), methicillin-sensitive *Staphylococcus aureus* (MSSA), methicillin-resistant *Staphylococcus epidermidis* (MRSE), methicillin-sensitive *Staphylococcus aureus* (MSSE), *Enterococcus faecium*, *Enterococcus faecalis*, *streptococcus pneumoniae*. Obtained from: Qianfoshan Hospital, First People's Hospital of Yunnan Province, Renji Hospital of Shanghai, People's Hospital of Jilin Province, Southwest Hospital.

Test results illustrate that, compared with linezolid, the compounds of the present invention all have higher antibacterial activity to the strains for test, and the differences are significant, indicating better clinical application potential of the compounds of the present invention.

Example 2

In Vivo Pharmacokinetics Tests on Rat of the Compounds of the Present Invention

Test Compound
Compounds 2, 3, 5, 7, 9, prepared by the processes in the examples, dissolved in physiological saline.

| Test animal | | | | |
|---|---|---|---|---|
| Test compound | Animal | Quantity | Body weight | Obtained from |
| Compound 2 | Male SD rat | 6 | 230-240 g | Beijing |
| Compound 3 | Male SD rat | 6 | 210-220 g | Weitonglihua |
| Compound 5 | Male SD rat | 6 | 260-280 g | Lab Animals |
| Compound 7 | Male SD rat | 6 | 220-240 g | Technology |
| Compound 9 | Male SD rat | 6 | 190-210 g | Ltd. |

Experiment Procedure
Administration
Administration is performed as described in the table below, fasting without water deprivation for 16 hours before administration, providing food 4 hours after the administration.

| Test compound | Administration Manner | Administration Dose | Administration Volume |
|---|---|---|---|
| Compound 2 | I.V | 1 mg/kg | 2 mL/kg |
|  | P.O | 2 mg/kg | 4 mL/kg |
| Compound 3 | I.V | 0.75 mg/kg | 2 mL/kg |
|  | P.O | 1 mg/kg | 2 mL/kg |
| Compound 5 | I.V | 1 mg/kg | 2 mL/kg |
|  | P.O | 2 mg/kg | 4 mL/kg |

-continued

| Test compound | Administration Manner | Administration Dose | Administration Volume |
|---|---|---|---|
| Compound 7 | I.V | 1 mg/kg | 2 mL/kg |
| | P.O | 2 mg/kg | 4 mL/kg |
| Compound 9 | I.V | 1 mg/kg | 2 mL/kg |
| | P.O | 2 mg/kg | 4 mL/kg |

I.V representing administration by intravenous push
P.O representing administration by lavage Blood Collection I.V: blood collection was carried out according to the time points in the table below. At each time point about 100 μl whole blood was collected into a heparin sodium anticoagulation tube, centrifuged at 4° C. in a low temperature high speed centrifuge at 8000 rpm for 6 minutes. Plasma was separated and stored frozen in a freezer at −80° C.

| Test compound | Administration Manner | Time points for blood collection |
|---|---|---|
| Compound 2 | I.V | 5 min, 15 min, 30 min, 1 h, 2 h, 4 h, 6 h, 8 h, 24 h, 30 h after administration |
| | P.O | 10 min, 30 min, 1 h, 2 h, 4 h, 6 h, 8 h, 24 h, 30 h after administration |
| Compound 3 | I.V | 0 min before administration, 5 min, 15 min, 30 min, 1 h, 2 h, 4 h, 6 h, 8 h, 24 h, 30 h after administration |
| | P.O | 0 min before administration, 5 min, 15 min, 30 min, 1 h, 2 h, 4 h, 6 h, 8 h, 24 h, 30 h after administration |
| Compound 5 | I.V | 5 min, 15 min, 30 min, 1 h, 2 h, 4 h, 6 h, 8 h, 24 h after administration |
| | P.O | 10 min, 30 min, 1 h, 2 h, 4 h, 6 h, 8 h, 24 h after administration |
| Compound 7 | I.V | 5 min, 15 min, 30 min, 1 h, 2 h, 4 h, 6 h, 8 h, 24 h after administration |
| | P.O | 10 min, 30 min, 1 h, 2 h, 4 h, 6 h, 8 h, 24 h after administration |
| Compound 9 | I.V | 5 min, 15 min, 30 min, 1 h, 2 h, 4 h, 6 h, 8 h, 24 h after administration |
| | P.O | 10 min, 30 min, 1 h, 2 h, 4 h, 6 h, 8 h, 24 h after administration |

Analysis of Plasma Sample

Compound 5, 7, 9: 20 μl plasma was each taken and added into 100 μl of Torezolid (TR-700) solution in methanol at a concentration of 50 ng/ml, mixed under vortex for 5 minutes, centrifuged at 12000 rpm for 5 minutes; 100 μl of supernatant was taken and added into 100 μl water, mixed under vortex for 2 minutes, and analyzed by using LC-MS/MS.

Compound 2: 20 μl plasma was taken and added into 100 μl of Radezolid solution in methanol at a concentration of 50 ng/ml, mixed under vortex for 3 minutes, centrifuged at 12000 rpm for 5 minutes; 100 μl of supernatant was taken and added into 100 μl water, mixed under vortex for 2 minutes, and analyzed by using LC-MS/MS.

Compound 3: 20 μl plasma was taken and added into 800 μl of KBP-3957 methyl tert-butyl ether solution at a concentration of 10 ng/ml, mixed under vortex for 10 minutes, centrifuged at 12000 rpm for 5 minutes; 400 μl of supernatant was taken and added into a 96-well plate, purged to dryness by nitrogen, 200 μl of methanol:water (7:3) solution was added, mixed under vortex for 10 minutes, and analyzed by using LC-MS/MS.

Tracing Detection

Compound 2 is the prodrug of compound 1. Compound 5 is the prodrug of compound 4. Compound 7 is the prodrug of compound 6. Compound 9 is the prodrug of compound 8. Thus, PK data of active compounds, i.e. compounds 1, 4, 6, 8, were detected after administration, respectively.

Calculation Formula $$\text{Absolute bioavailability } F\% = [AUC]_{INF(PO)} * Dose_{(IV)} / [AUC]_{INF(IV)} * Dose_{(PO)}$$

Test Results

See Tables 3, 4.

TABLE 3

PK evaluation results (I.V) on rat of the compounds of the present invention

| Test compound | Detect compound | Dose (mg/kg) | $AUC_{inf}$ (ng/mL/h) | Vss (L/kg) | $T_{1/2}$ (h) | CL (L/kg/h) |
|---|---|---|---|---|---|---|
| Compound 2 | Compound 1 | 1 | 986 | 0.80 | 0.84 | 1.02 |
| Compound 3 | Compound 3 | 0.75 | 11597 | 0.37 | 5.29 | 0.07 |
| Compound 5 | Compound 4 | 1 | 1874 | 0.44 | 1.42 | 0.54 |
| Compound 7 | Compound 6 | 1 | 2468 | 0.53 | 1.11 | 0.41 |
| Compound 9 | Compound 8 | 1 | 3499 | 0.40 | 1.19 | 0.29 |

TABLE 4

PK evaluation results (P.O) on rat of the compounds of the present invention

| Test compound | Detect compound | Dose (mg/kg) | $AUC_{inf}$ (ng/mL/h) | $C_{max}$ (ng/mL) | $T_{max}$ (h) | $T_{1/2}$ (h) | F % |
|---|---|---|---|---|---|---|---|
| Compound 2 | Compound 1 | 2 | 1393 | 844 | 0.5 | 1.17 | 71.1 |
| Compound 3 | Compound 3 | 1 | 7029 | 614 | 4 | 5.55 | 45.5 |
| Compound 5 | Compound 4 | 2 | 1781 | 1028 | 0.5 | 1.52 | 47.5 |
| Compound 7 | Compound 6 | 2 | 4202 | 1670 | 1 | 1.29 | 85.1 |
| Compound 9 | Compound 8 | 2 | 5812 | 1375 | 0.5 | 2.67 | 83.1 |

$AUC_{inf}$ representing the area under the drug concentration in the plasma versus time curve$_{0 \to \infty}$ CL representing clearance Vss representing apparent volume of distribution $T_{1/2}$ representing half-life $T_{max}$ representing peak time of drug in plasma $C_{max}$ representing peak concentration of drug in plasma F % representing absolute bioavailability Test Results It can be seen from Tables 3, 4 that the compounds of the present invention have good pharmacokinetic properties and are suitable for drug use.

Specific Embodiments

The above content of the present invention is further illustrated in detail by the specific embodiments as examples below. However, it should not be interpreted as that the scope of the above subjects of the present invention is only limited to the examples below. Any technology achieved based on the above content of the present invention is encompassed by the present invention.

Example 1

Preparation of (R)-3-(3-fluoro-4-(6-((2-methyl-2H-tetrazol-5-yl)amino)-pyridin-3-yl)phenyl)-5-(hydroxylmethyl)oxazolidin-2-one (Compound 1)

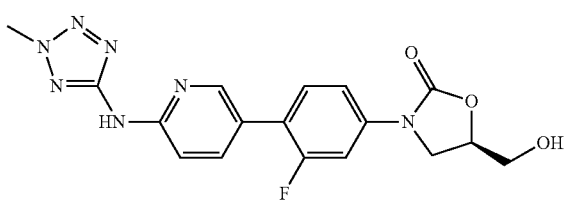 [SMILES: Cn1nnc(Nc2ccc(-c3ccc(N4C[C@H](CO)OC4=O)cc3F)cn2)n1]

(1) Preparation of 5-bromo-N-(2-methyl-2H-tetrazol-5-yl)pyridine-2-amine

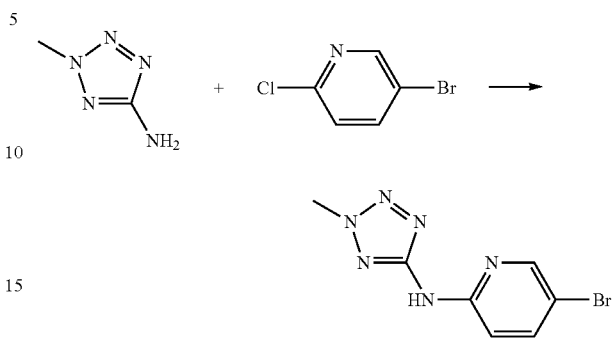

2-methyl-2H-tetrazole-5-amine (7.7 g, 78 mmol), 2-chloro-5-bromopyridine (10 g, 52 mmol), and potassium tert-butylate (11.6 g, 104 mmol) were dissolved in 100 mL THF, heated under reflux and reacted for 12 h. Water was added, extracted with ethyl acetate, and the organic phase was dried, concentrated, and the solid was separated by a silica gel column (dichloromethane:methanol=100:1) to obtain 5-bromo-N-(2-methyl-2H-tetrazol-5-yl)pyridine-2-amine 200 mg, at a yield of 1.5%.

(2) Preparation of (R)-3-(3-fluoro-4-(6-((2-methyl-2H-tetrazol-5-yl)amino)pyridin-3-yl)phenyl)-5-(hydroxylmethyl)oxazolidin-2-one

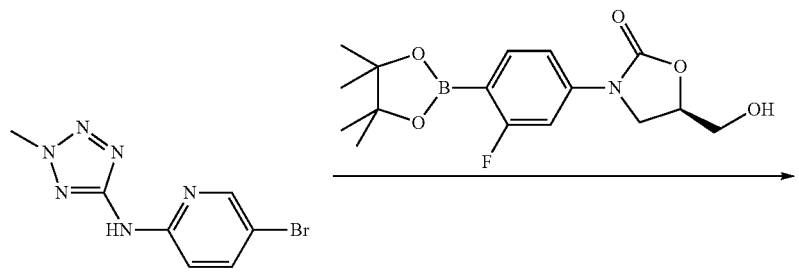

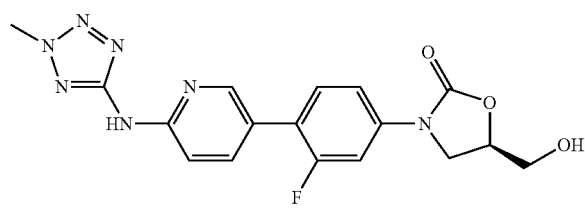

5-bromo-N-(2-methyl-2H-tetrazol-5-yl)pyridine-2-amine (200 mg, 0.78 mmol), (R)-3-(3-fluoro-4-(4,4,5,5-tetramethyl-1,3,2-dioxaborolan-2-yl)phenyl)-5-(hydroxylmethyl)oxazolidin-2-one (317 mg, 0.94 mmol), cesium carbonate (508 mg, 1.56 mmol) and Pd(dppf)Cl$_2$ (90 mg, 0.16 mmol) were dissolved in 16 mL dioxane and 4 mL water, heated to 100° C. and reacted for 6 h. The solvent was evaporated to dryness, and the solid was separated by a silica gel column (dichloromethane:methanol=40:1) to obtain (R)-3-(3-fluoro-4-(6-((2-methyl-2H-tetrazol-5-yl)amino)pyridin-3-yl)phenyl)-5-(hydroxylmethyl)oxazolidin-2-one 90 mg, at a yield of 30%.

Molecular formula: C$_{17}$H$_{16}$FN$_7$O$_3$ Mass spectrum (m/e): 386.2 (M+1)

$^1$H NMR: (400 MHz, DMSO-d$_6$) δ 10.48 (s, 1H), 8.42 (s, 1H), 7.93 (d, 1H), 7.65 (d, 1H), 7.60 (m, 2H), 7.44 (d, 1H), 5.24 (m, 1H), 4.73 (m, 1H), 4.29 (s, 3H), 4.12 (t, 1H), 3.87 (m, 1H), 3.67 (m, 1H), 3.58 (m, 1H).

Example 2

Preparation of (S)—N-((3-(3-fluoro-4-(6-((2-methyl-2H-tetrazol-5-yl)amino)pyridin-3-yl)phenyl)-2-oxooxazolidin-5-yl)methyl)acetamide (Compound 3)

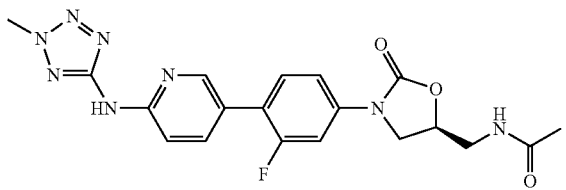 [SMILES: CC(=O)NC[C@H]1CN(c2ccc(-c3ccc(Nc4nnn(C)n4)nc3)c(F)c2)C(=O)O1]

(1) Preparation of (S)—N-((3-(3-fluoro-4-(4,4,5,5-tetramethyl-1,3,2-dioxaborolan-2-yl)phenyl)-2-oxooxazolidin-5-yl)methyl)acetamide

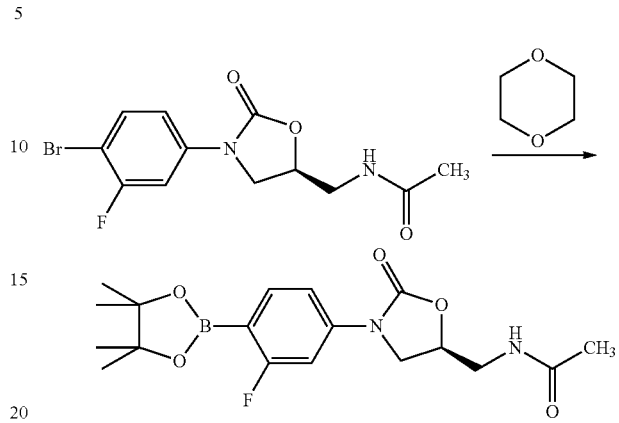

Into a dry reaction flask were added 30 mL 1,4-dioxane, 3.31 g (10 mmol) (S)—N-((3-(3-fluoro-4-bromophenyl)-2-oxooxazolidin-5-yl)methyl)acetamide, 2.54 g (10 mmol) bis(pinacolato)diborolane, and 0.98 g (10 mmol) potassium acetate, and into which argon was introduced. Then 0.3 g Pd(PPh$_3$)$_2$Cl$_2$ was added, and continued to introduce argon into the reaction solution. The reaction was stirred at 90° C. overnight. The resulted reaction mixture was cooled to room temperature, filtered through diatomite, and extracted with ethyl acetate and saline. The organic phase was dried over anhydrous sodium sulfate, and concentrated. A grey solid precipitated, and was filtered to obtain 3.22 g of product, at a yield of 85.2%.

(2) Preparation of (S)—N-((3-(3-fluoro-4-(6-(2-methyl-2H-tetrazol-5-ylamino)pyridine-3-yl)phenyl)-2-oxooxazolidin-5-yl)methyl)acetamide

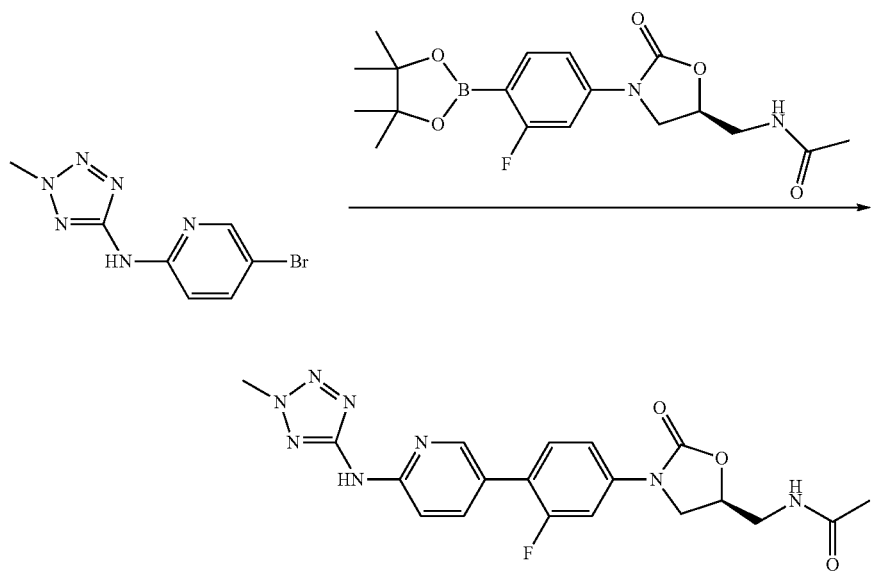

The procedure was the same as Example 1(2) with the exception of using (S)—N-((3-(3-fluoro-4-(4,4,5,5-tetramethyl-1,3,2-dioxaborolan-2-yl)phenyl)-2-oxooxazolidin-5-yl)methyl)acetamide instead of (R)-3-(3-fluoro-4-(4,4,5,5-tetramethyl-1,3,2-dioxaborolan-2-yl)phenyl)-5-(hydroxylmethyl)oxazolidin-2-one, at a yield of 15%.

Molecular formula: $C_{19}H_{19}FN_8O_3$ Mass spectrum (m/e): 427.2 (M+1)

$^1$H NMR: (400 MHz, DMSO-$d_6$) δ 10.48 (s, 1H), 8.42 (s, 1H), 8.25 (t, 1H), 7.93 (d, 1H), 7.75 (d, 1H), 7.62 (m, 2H), 7.40 (d, 1H), 4.77 (m, 1H), 4.29 (s, 3H), 4.16 (t, 1H), 3.78 (m, 1H), 3.37 (t, 2H), 1.81 (s, 3H).

Example 3

Preparation of (R)-3-(3-fluoro-4-(6-((1-methyl-1H-tetrazol-5-yl)amino)pyridin-3-yl)phenyl)-5-(hydroxylmethyl)oxazolidin-2-one (Compound 4)

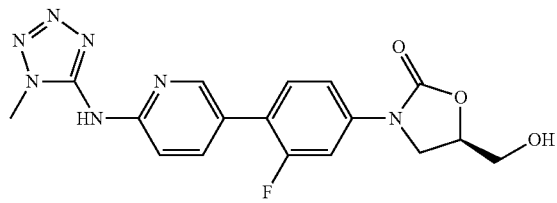 [SMILES: Cn1nnnc1Nc1ccc(-c2ccc(N3C[C@H](CO)OC3=O)cc2F)cn1]

(1) Preparation of 5-bromo-N-(1-methyl-1H-tetrazol-5-yl)pyridine-2-amine

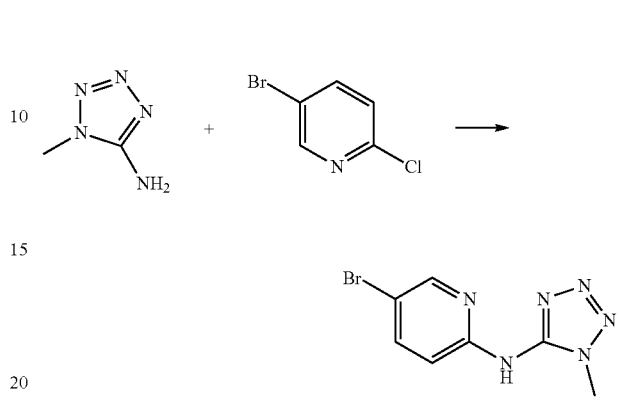

The procedure was the same as Example 1(1) with the exception of using 1-methyl-1H-tetrazole-5-amine instead of 2-methyl-2H-tetrazole-5-amine, at a yield of 33%.

(2) Preparation of (R)-3-(3-fluoro-4-(6-((1-methyl-1H-tetrazol-5-yl)amino)pyridin-3-yl)phenyl)-5-(hydroxylmethyl)oxazolidin-2-one

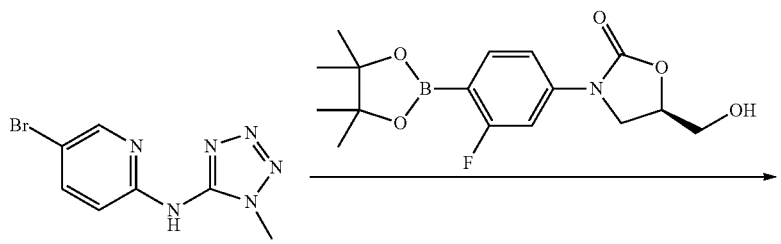

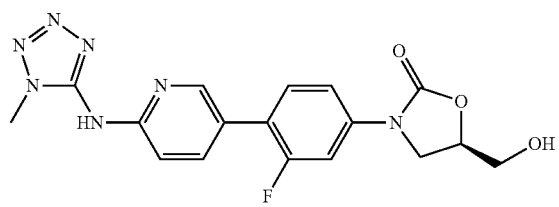

The procedure was the same as Example 1(2) with the exception of using 5-bromo-N-(1-methyl-1H-tetrazol-5-yl) pyridine-2-amine instead of 5-bromo-N-(2-methyl-2H-tetrazol-5-yl)pyridine-2-amine, at a yield of 11%.

Molecular formula: $C_{17}H_{16}FN_7O_3$ Mass spectrum (m/e): 386.2 (M+1)

$^1$H-NMR (400 MHz, DMSO): δ 3.32-3.56 (m, 1H), 3.58-3.71 (m, 1H), 3.85-3.87 (m, 1H), 3.95 (S, 3H), 4.10-4.15 (t, 1H), 4.72-4.74 (t, 1H), 5.23-5.25 (t, 1H), 7.44-7.46 (t, 1H), 7.60-7.66 (m, 2H), 7.81-7.84 (d, 1H), 7.98-8.01 (d, 1H), 8.46 (s, 1H), 10.38 (s, 1H)

Example 4

Preparation of (R)-(3-(3-fluoro-4-(6-((1-methyl-1H-tetrazol-5-yl)amino)pyridin-3-yl)phenyl)-2-oxooxazolidin-5-yl)methyl phosphate disodium salt (Compound 5)

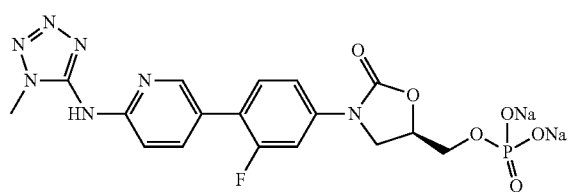

(1) Preparation of (R)-(3-(3-fluoro-4-(6-((1-methyl-1H-tetrazol-5-yl)amino)pyridin-3-yl)phenyl)-2-oxooxazolidin-5-yl)methyl dihydrogen phosphate

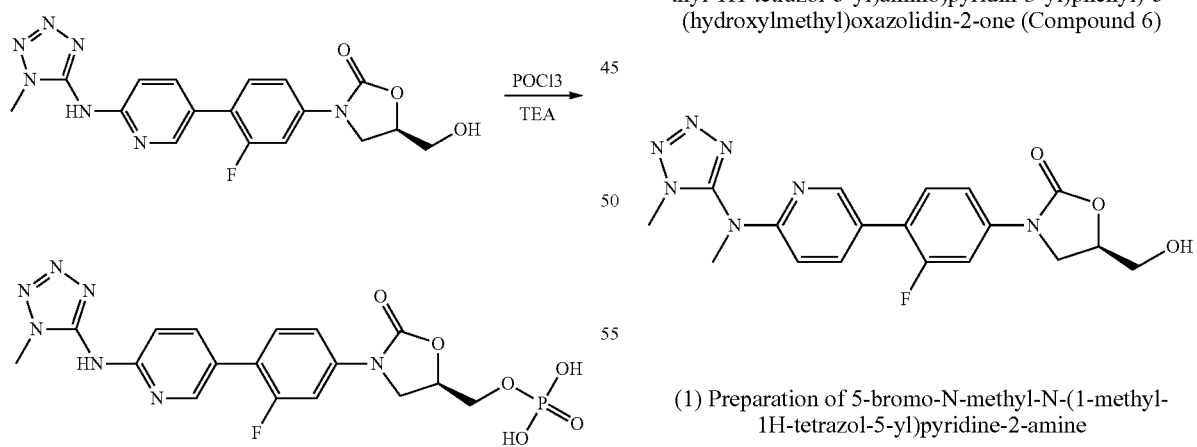

(R)-3-(3-fluoro-4-(6-((1-methyl-1H-tetrazol-5-yl)amino) pyridin-3-yl)phenyl)-5-(hydroxylmethyl)oxazolidin-2-one (200 mg, 0.52 mmol) was dissolved in 30 mL THF, and triethylamine (262 mg, 2.6 mmol) was added under ice-water bath. After half an hour, phosphorus oxychloride (397 mg, 2.6 mmol) was added, and reacted at room temperature for 12 h. Water (180 mg, 10 mmol) was added dropwise. After filtration, 140 mg of product was obtained, at a yield of 57%.

(2) Preparation of (R)-(3-(3-fluoro-4-(6-((1-methyl-1H-tetrazol-5-yl)amino)pyridin-3-yl)phenyl)-2-oxooxazolidin-5-yl)methyl phosphate disodium salt

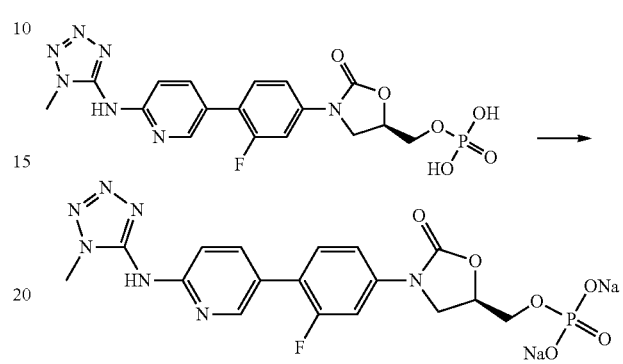

(R)-(3-(3-fluoro-4-(6-((1-methyl-1H-tetrazol-5-yl) amino)pyridin-3-yl)phenyl)-2-oxooxazolidin-5-yl)methyl dihydrogen phosphate (140 mg, 0.3 mmol) was dissolved in 15 mL methanol. Sodium methoxide (48 mg, 0.9 mmol) was added, and reacted at room temperature for 12 h. After filtration 110 mg of product was obtained, at a yield of 71.6%.

Molecular formula: $C_{17}H_{15}FN_7Na_2O_6P$ Mass spectrum (m/e): 466.0 (M+1)

$^1$H-NMR (400 MHz, DMSO): δ 3.88-3.90 (m, 1H), 3.95 (S, 3H), 4.02-4.09 (m, 2H), 4.19 (t, 1H), 4.93 (s, 1H), 7.43-7.45 (d, 1H), 7.62-7.68 (m, 2H), 7.96-7.98 (d, 1H), 8.13 (3, 1H), 8.23-8.26 (d, 1H), 8.53 (d, 1H)

Example 5

Preparation of (R)-3-(3-fluoro-4-(6-(methyl(1-methyl-1H-tetrazol-5-yl)amino)pyridin-3-yl)phenyl)-5-(hydroxylmethyl)oxazolidin-2-one (Compound 6)

(1) Preparation of 5-bromo-N-methyl-N-(1-methyl-1H-tetrazol-5-yl)pyridine-2-amine

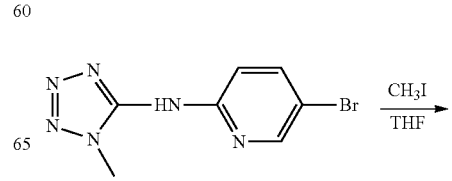

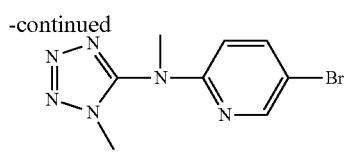

5-bromo-N-(1-methyl-1H-tetrazol-5-yl)pyridine-2-amine (1 g, 3.9 mmol) was dissolved in 50 mL THF, potassium tert-butylate (0.88 g, 7.8 mmol) and iodomethane (1.1 g, 7.8 mmol) were added slowly. The reaction was heated to 70° C. and reacted for 12 h. After filtration and concentration, 330 mg of product was obtained by separation on a silica gel column (dichloromethane:methanol=100:1), at a yield of 31%.

(2) Preparation of (R)-3-(3-fluoro-4-(6-(methyl(1-methyl-1H-tetrazol-5-yl)amino)pyridin-3-yl)phenyl)-5-(hydroxylmethyl)oxazolidin-2-one

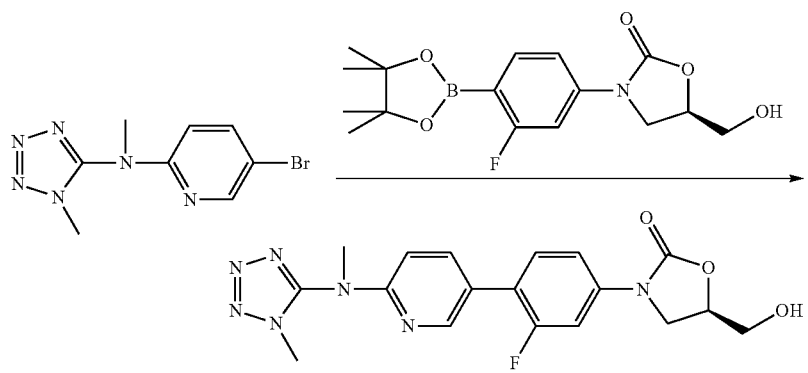

The procedure was the same as Example 1 (2) with the exception of using 5-bromo-N-methyl-N-(1-methyl-1H-tetrazol-5-yl)pyridine-2-amine instead of 5-bromo-N-(2-methyl-2H-tetrazol-5-yl)pyridine-2-amine, at a yield of 24%.

Molecular formula: $C_{18}H_{18}FN_7O_3$ Mass spectrum (m/e): 400.2 (M+1)

$^1$H-NMR (400 MHz, DMSO): δ 3.45 (s, 3H), 3.57 (m, 1H), 3.66 (m, 1H), 3.76 (S, 3H), 3.84-3.88 (t, 1H), 4.09-4.11 (t, 1H), 4.72-4.73 (t, 1H), 5.22-5.25 (t, 1H), 7.15-7.17 (d, 1H), 7.42-7.45 (d, 1H), 7.56-7.65 (m, 2H), 7.96-7.99 (d, 1H), 8.36 (s, 1H)

Example 6

Preparation of (R)-(3-(3-fluoro-4-(6-(methyl(1-methyl-1H-tetrazol-5-yl)amino)pyridin-3-yl)phenyl)-2-oxooxazolidin-5-yl)methyl phosphate disodium salt (Compound 7)

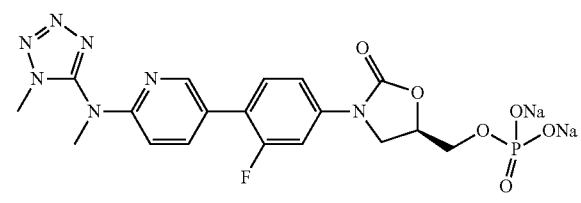

(1) Preparation of (R)-(3-(3-fluoro-4-(6-(methyl(1-methyl-1H-tetrazol-5-yl)amino)pyridin-3-yl)phenyl)oxazolidin-2-one-5-yl)methyl dihydrogen phosphate

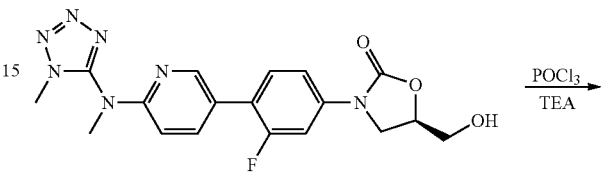

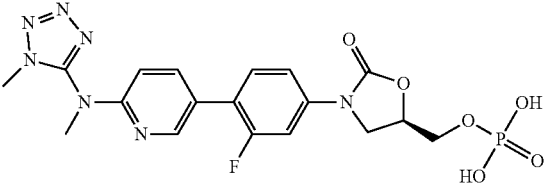

The procedure was the same as Example 4 (1) with the exception of using (R)-3-(3-fluoro-4-(6-(methyl(1-methyl-1H-tetrazol-5-yl)amino)pyridin-3-yl)phenyl)-5-(hydroxylmethyl)oxazolidin-2-one instead of (R)-3-(3-fluoro-4-(6-((1-methyl-1H-tetrazol-5-yl)amino)pyridin-3-yl)phenyl)-5-(hydroxylmethyl)oxazolidin-2-one, at a yield of 74%.

(2) Preparation of (R)-(3-(3-fluoro-4-(6-(methyl(1-methyl-1H-tetrazol-5-yl)amino)pyridin-3-yl)phenyl)-2-oxooxazolidin-5-yl)methyl phosphate disodium salt

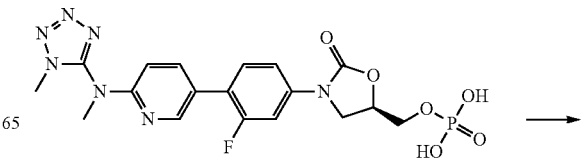

-continued

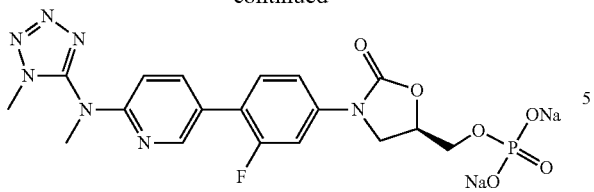

The procedure was the same as Example 4 (2) with the exception of using (R)-(3-(3-fluoro-4-(6-(methyl(1-methyl-1H-tetrazol-5-yl)amino)pyridin-3-yl)phenyl)-2-oxooxazolidin-5-yl)methyl dihydrogen phosphate instead of (R)-(3-(3-fluoro-4-(6-((1-methyl-1H-tetrazol-5-yl)amino)pyridin-3-yl)phenyl)-2-oxooxazolidin-5-yl)methyl dihydrogen phosphate, at a yield of 61%.

Molecular formula: $C_{18}H_{17}FN_7Na_2O_6P$ Mass spectrum (m/e): 480.0 (M+1)

$^1$H-NMR (400 MHz, DMSO): δ 3.47 (s, 3H), 3.75 (S, 3H), 3.85-3.89 (t, 1H), 4.01-4.08 (m, 2H), 4.15-4.20 (s, 1H), 7.15-7.17 (d, 1H), 7.40-7.43 (d, 1H), 7.57-7.63 (m, 2H), 7.96-7.99 (d, 1H), 8.31 (s, 1H), 8.34 (s, 1H)

Example 7

Preparation of (R)-3-(3-fluoro-4-(6-(methyl(2-methyl-2H-tetrazol-5-yl)amino)pyridin-3-yl)phenyl)-5-(hydroxylmethyl)oxazolidin-2-one (Compound 8)

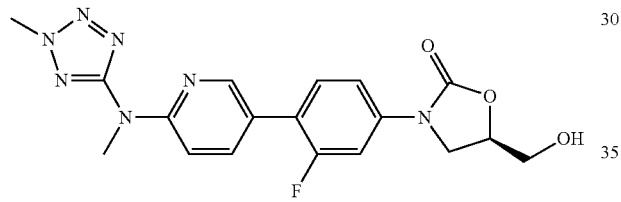

(1) Preparation of 5-bromo-N-methyl-N-(2-methyl-2H-tetrazol-5-yl)pyridine-2-amine

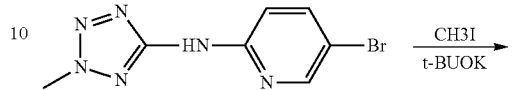

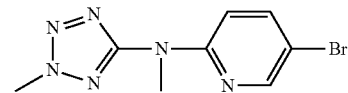

The procedure was the same as Example 5 (1) with the exception of using 5-bromo-N-(2-methyl-2H-tetrazol-5-yl)pyridine-2-amine instead of 5-bromo-N-(1-methyl-1H-tetrazol-5-yl)pyridine-2-amine, at a yield of 31%.

(2) Preparation of (R)-3-(3-fluoro-4-(6-(methyl(2-methyl-2H-tetrazol-5-yl)amino)pyridin-3-yl)phenyl)-5-(hydroxylmethyl)oxazolidin-2-one

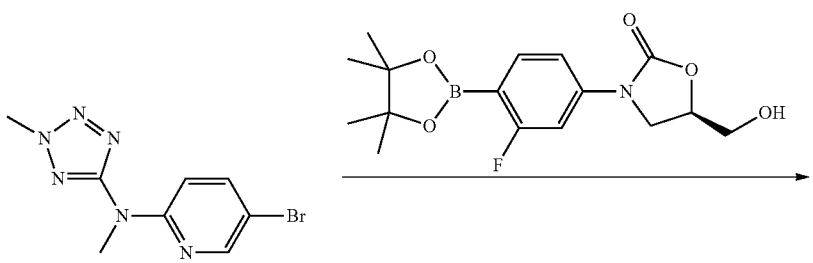

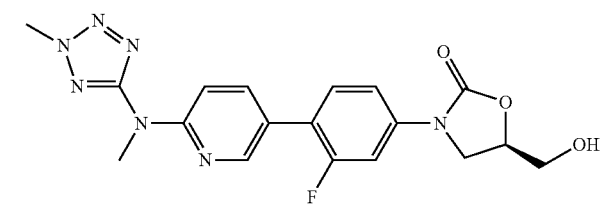

The procedure was the same as Example 1 (2) with the exception of using 5-bromo-N-methyl-N-(2-methyl-2H-tetrazol-5-yl)pyridine-2-amine instead of 5-bromo-N-(2-methyl-2H-tetrazol-5-yl)pyridine-2-amine, at a yield of 27%.

Molecular formula: $C_{18}H_{18}FN_7O_3$ Mass spectrum (m/e): 400.2 (M+1)

$^1$H-NMR (400 MHz, DMSO): δ 3.58 (d, 1H), 3.65 (m, 4H), 3.85-3.88 (m, 1H), 4.1-4.14 (t, 1H), 4.32 (s, 3H), 4.73-4.74 (t, 1H), 5.24 (s, 1H), 7.44-7.46 (d, 1H), 7.59-7.65 (m, 2H), 7.93-8.01 (d, 2H), 8.52 (s, 1H)

Example 8

Preparation of (R)-(3-(3-fluoro-4-(6-(methyl(2-methyl-2H-tetrazol-5-yl)amino)pyridin-3-yl)phenyl)-2-oxooxazolidin-5-yl)methyl phosphate disodium salt
(Compound 9)

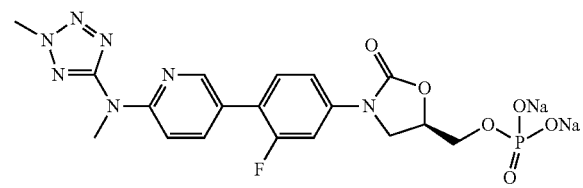

(1) Preparation of (R)-(3-(3-fluoro-4-(6-(methyl(2-methyl-2H-tetrazol-5-yl)amino)pyridin-3-yl)phenyl)-2-oxooxazolidin-5-yl)methyl dihydrogen phosphate

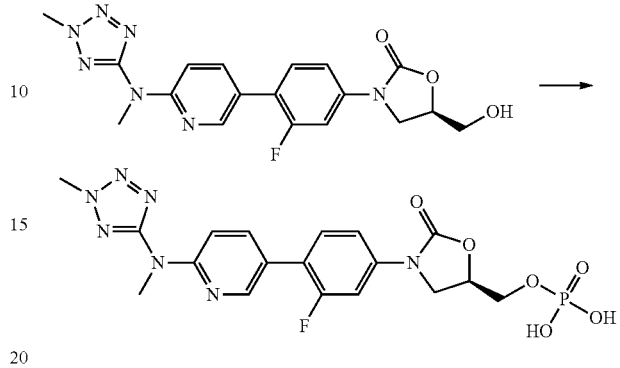

The procedure was the same as Example 4 (1) with the exception of using (R)-3-(3-fluoro-4-(6-(methyl(2-methyl-2H-tetrazol-5-yl)amino)pyridin-3-yl)phenyl)-5-(hydroxylmethyl)oxazolidin-2-one instead of (R)-3-(3-fluoro-4-(6-((1-methyl-1H-tetrazol-5-yl)amino)pyridin-3-yl)phenyl)-5-(hydroxylmethyl)oxazolidin-2-one, at a yield of 67%.

(2) Preparation of (R)-(3-(3-fluoro-4-(6-(methyl(2-methyl-2H-tetrazol-5-yl)amino)pyridin-3-yl)phenyl)-2-oxooxazolidin-5-yl)methyl phosphate disodium salt

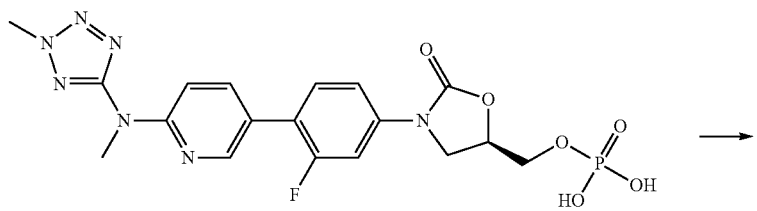

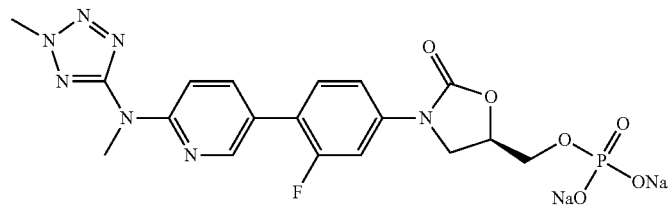

The procedure was the same as Example 4 (2) with the exception of using (R)-(3-(3-fluoro-4-(6-(methyl(2-methyl-2H-tetrazol-5-yl)amino)pyridin-3-yl)phenyl)-2-oxooxazolidin-5-yl)methyl dihydrogen phosphate instead of (R)-(3-(3-fluoro-4-(6-((1-methyl-1H-tetrazol-5-yl)amino)pyridin-3-yl)phenyl)-2-oxooxazolidin-5-yl)methyl dihydrogen phosphate, at a yield of 94%.

Molecular formula: $C_{18}H_{17}FN_7Na_2O_6P$ Mass spectrum (m/e): 480.0 (M+1)

$^1$H-NMR (400 MHz, DMSO): δ 3.196 (s, 3H), 3.84-4.02 (m, 4H), 4.19 (s, 3H), 4.84 (s, 1H), 7.08 (s, 1H), 7.21-7.24 (d, 2H), 7.41-7.43 (d, 1H), 7.85-7.861 (d, 1H), 8.13 (s, 1H)

Example 9

Preparation of (R)-3-(3-fluoro-4-(6-((1-methyl-1H-pyrazol-3-yl)amino)pyridin-3-yl)phenyl)-5-(hydroxylmethyl)oxazolidin-2-one (Compound 10)

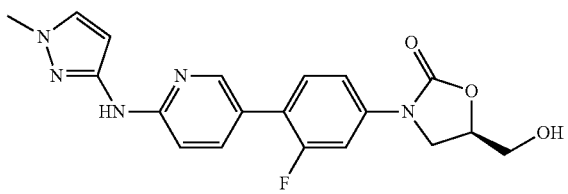 [SMILES: Cn1ccc(Nc2ccc(-c3ccc(N4C[C@H](CO)OC4=O)cc3F)cn2)n1]

(1) Preparation of 5-bromo-N-(1-methyl-1H-pyrazol-3-yl)pyridine-2-amine

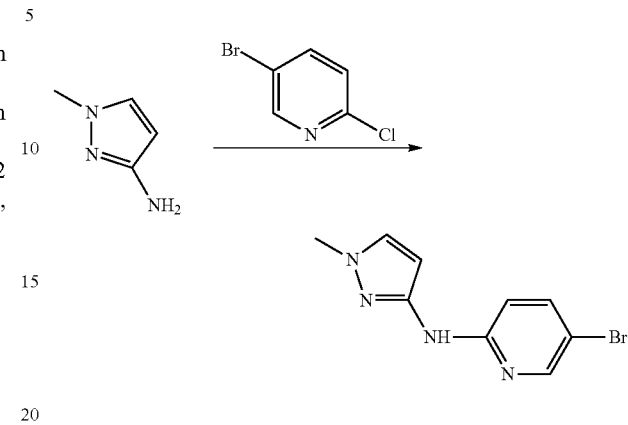

The procedure was the same as Example 1 (1) with the exception of using 1-methyl-1H-pyrazole-3-amine instead of 2-methyl-2H-tetrazole-5-amine, at a yield of 9%.

(2) Preparation of (R)-3-(3-fluoro-4-(6-(1-methyl-1H-pyrazol-3-yl)amino)pyridin-3-yl)phenyl)-5-(hydroxylmethyl)oxazolidin-2-one The procedure was the same as Example 1 (2) with the exception of using 5-bromo-N-(1-methyl-1H-pyrazol-3-yl)pyridine-2-amine instead of 5-bromo-N-(2-methyl-2H-tetrazol-5-yl)pyridine-2-amine, at a yield of 16%.

Molecular formula: C$_{19}$H$_{18}$FN$_5$O$_3$ Mass spectrum (m/e): 384.2 (M+1)

$^1$H-NMR (400 MHz, DMSO): δ 3.573-3.574 (m, 1H), 3.774 (m, 1H), 3.737 (s, 3H), 3.85-3.87 (t, 1H), 4.089-4.11 (t, 1H), 4.72-4.73 (m, 1H), 5.22-5.25 (t, 1H), 6.29-6.30 (s, 1H), 7.31-7.33 (d, 1H), 7.31-7.33 (d, 1H), 7.39-7.72 (m, 3H), 7.72-7.75 (d, 1H), 8.28 (s, 1H), 9.39 (s, 1H)

Example 10

Preparation of (R)-3-(3-fluoro-4-(6-((1-methyl-1H-1,2,3-triazol-5-yl)amino)pyridin-3-yl)phenyl)-5-(hydroxymethyl)oxazolidin-2-one (Compound 11a)

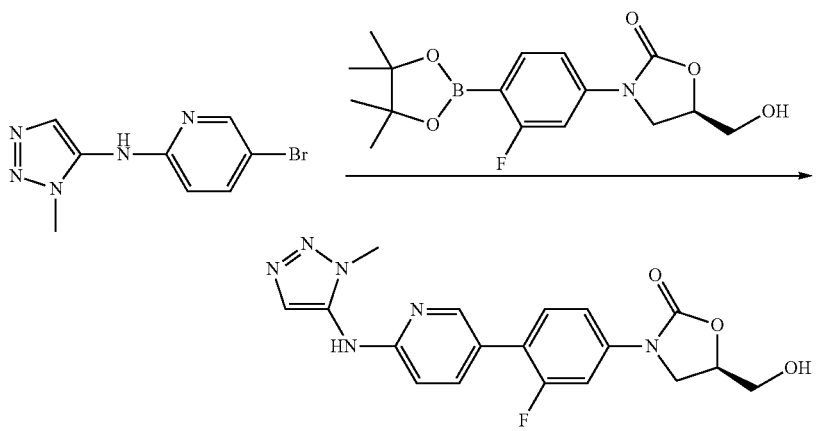

The procedure was the same as Example 1 (2) with the exception of using 5-bromo-N-(1-methyl-1H-1,2,3-triazol-5-yl)pyridine-2-amine instead of 5-bromo-N-(2-methyl-2H-tetrazol-5-yl)pyridine-2-amine, at a yield of 11%.

Molecular formula: C$_{18}$H$_{17}$FN$_6$O$_3$ Mass spectrum (m/e): 385.2 (M+1)

$^1$H NMR (DMSO-d6): δ 9.86 (s, 1H), 8.36 (s, 1H), 7.91 (m, 1H), 7.78 (d, 1H), 7.57 (m, 2H), 7.42 (d, 1H), 7.10 (d, 1H), 5.24 (s, 1H), 4.73 (m, 1H), 4.21 (s, 1H), 4.08 (s, 3H), 3.86 (m, 1H), 3.67 (m, 1H), 3.57 (m, 1H)

Compound 11 can also be prepared according to the process for preparing Compound 11a.

Example 11

Preparation of (R)-3-(3-fluoro-4-(6-((2-methyl-2H-1,2,3-triazol-4-yl)amino)pyridin-3-yl)phenyl)-5-(hydroxylmethyl)oxazolidin-2-one (Compound 12)

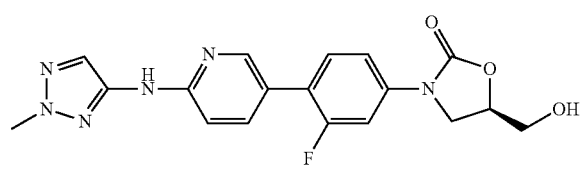 [SMILES: Cn1ncc(Nc2ccc(-c3ccc(N4C[C@H](CO)OC4=O)cc3F)cn2)n1]

(1) Preparation of 5-bromo-N-(2-methyl-2H-1,2,3-triazol-4-yl)pyridine-2-amine

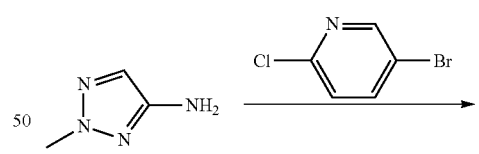

The procedure was the same as Example 1 (1) with the exception of using 2-methyl-2H-1,2,3-triazol-4-amine instead of 2-methyl-2H-tetrazole-5-amine, at a yield of 50%.

(2) Preparation of (R)-3-(3-fluoro-4-(6-((2-methyl-2H-1,2,3-triazol-4-yl)amino)pyridin-3-yl)phenyl)-5-(hydroxylmethyl)oxazolidin-2-one

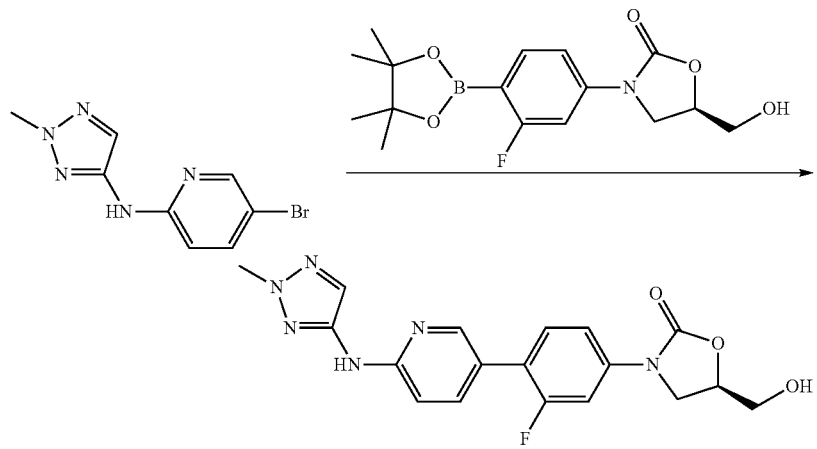

The procedure was the same as Example 1 (2) with the exception of using 5-bromo-N-(2-methyl-2H-1,2,3-triazol-4-yl)pyridine-2-amine instead of 5-bromo-N-(2-methyl-2H-tetrazol-5-yl)pyridine-2-amine, at a yield of 11%.

Molecular formula: $C_{18}H_{17}FN_6O_3$ Mass spectrum (m/e): 385.2 (M+1)

$^1$H NMR (DMSO-d6): δ 9.92 (s, 1H), 8.33 (s, 1H), 8.19 (m, 1H), 7.75 (d, 1H), 7.58 (m, 2H), 7.43 (t, 1H), 6.99 (d, 1H), 5.25 (s, 1H), 4.73 (m, 1H), 4.12 (s, 1H), 4.01 (s, 3H), 3.86 (m, 1H), 3.68 (m, 1H), 3.56 (m, 1H)

Example 12

Preparation of 3-(4-(6-((1H-1,2,3-triazol-4-yl)amino)pyridin-3-yl)-3-fluorophenyl)-5-(hydroxylmethyl)oxazolidin-2-one (Compound 13a)

1) Preparation of 1-(methoxymethyl)-4-nitro-1H-1,2,3-triazole

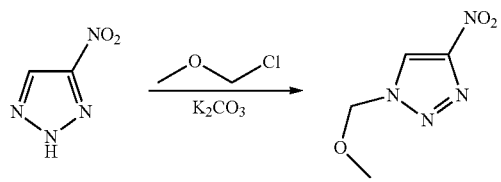

4-nitro-1H-1,2,3-triazole (6.468 g, 56.707 mmol) and potassium carbonate (15.683 g, 113.472 mmol) were added into 150 mL acetone. Chloromethyl methyl ether (4.74 mL, 62.407 mmol) was added dropwise into the above mixture under ice bath. After completion, water and ethyl acetate were added into the reaction solution. Phases were separated. The aqueous phase was extracted with ethyl acetate. The organic phases were combined, washed with saturated sodium chloride, dried over anhydrous sodium sulfate, filtered, concentrated, chromatographed on a silica gel column (ethyl acetate: petroleum ether=1:5) to obtain 1-(methoxymethyl)-4-nitro-1H-1,2,3-triazole, as 5.517 g of a light yellow liquid, at a yield of 61.5%.

2) Preparation of 1-(methoxymethyl)-4-amino-1H-1,2,3-triazole

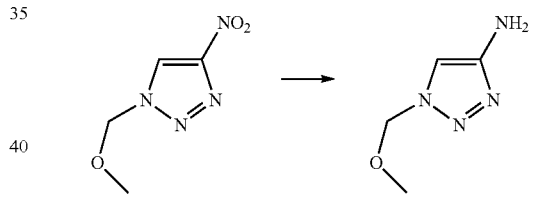

1-(methoxymethyl)-4-nitro-1H-1,2,3-triazole (5.517 g, 34.891 mmol), zinc powder (22.697 g, 349.185 mmol) and ammonium chloride (18.678 g, 349.187 mmol) were added successively into a mixed solvent of methanol (100 mL) and tetrahydrofuran (100 mL), and stirred for 18 hours. The insoluble was removed by suction filtration. After concentration, 1-(methoxymethyl)-4-amino-1H-1,2,3-triazole was obtained as 3.56 g of a brown-yellow oil, at a yield of 79.6%.

3) Preparation of 5-bromo-N-(1-(methoxymethyl)-1H-1,2,3-triazol-4-yl)pyridine-2-amine

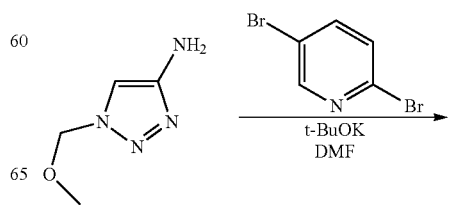

-continued

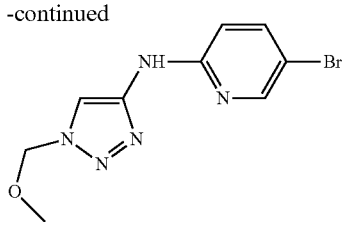

1-(methoxymethyl)-4-amino-1H-1,2,3-triazole (3.56 g, 27.784 mmol), 2,5-dibromopyridine (19.608 g, 82.773 mmol) and potassium tert-butylate (9.345 g, 83.252 mmol) were added into DMF (100 mL), heated to 70° C., and stirred for 72 hours. The reaction solution was poured into water, and extracted with ethyl acetate. The combined organic phase was washed with a saturated solution of sodium chloride, dried over anhydrous sodium sulfate, concentrated, and separated on a silica gel column chromatograph (ethyl acetate:petroleum ether=1:30) to obtain 0.318 g of 5-bromo-N-(1-(methoxymethyl)-1H-1,2,3-triazol-4-yl)pyridine-2-amine as a yellow solid, at a yield of 4%.

4) 3-(3-fluoro-4-(6-((1-(methoxymethyl)-1H-1,2,3-triazol-4-yl)amino)pyridin-3-yl)phenyl)-5-(hydroxylmethyl)oxazolidin-2-one 5) Preparation of 3-(4-(6-((1H-1,2,3-triazol-4-yl)amino)pyridin-3-yl)-3-fluorophenyl)-5-(hydroxylmethyl)oxazolidin-2-one

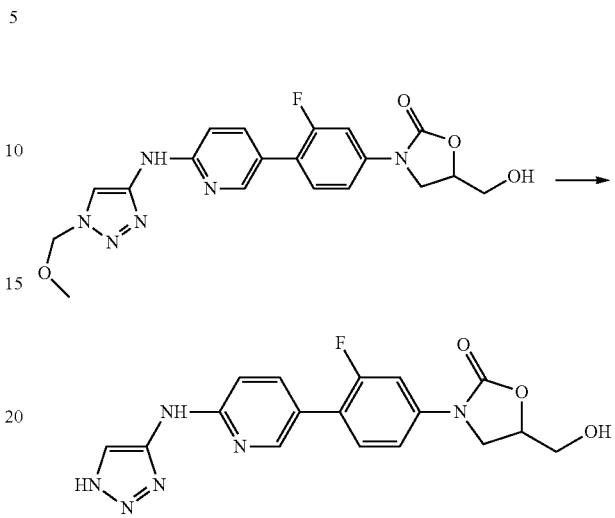

The crude 3-(3-fluoro-4-(6-((1-(methoxymethyl)-1H-1,2,3-triazol-4-yl)amino)pyridine-3-yl)phenyl)-5-(hydroxylm-

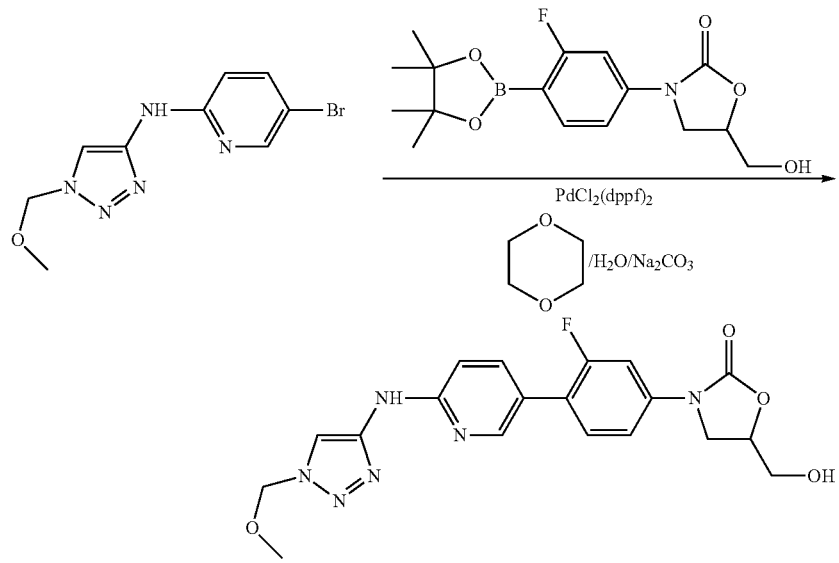

5-bromo-N-(1-(methoxymethyl)-1H-1,2,3-triazol-4-yl)pyridine-2-amine (0.318 g, 1.119 mmol), 3-(3-fluoro-4-(4,4,5,5-tetramethyl-1,3,2-dioxaborolan-2-yl)phenyl)-5-(hydroxylmethyl)oxazolidin-2-one (0.852 g, 2.527 mmol), sodium carbonate (0.357 g, 3.368 mmol), PdCl$_2$(dppf)$_2$ (0.064 g) were added into 20 mL dioxane and 2 drops of water, refluxed and reacted for 18 h under protection of nitrogen, cooled to room temperature, filtered, concentrated, chromatographed on a silica gel column (CH$_3$OH:CH$_2$Cl$_2$=1:25), to obtain 0.709 g of crude 3-(3-fluoro-4-(6-((1-(methoxymethyl)-1H-1,2,3-triazol-4-yl)amino)pyridin-3-yl)phenyl)-5-(hydroxylmethyl)oxazolidin-2-one.

ethyl)oxazolidin-2-one obtained in the last step was dissolved in 20 mL tetrahydrofuran. Into the solution were added 20 mL of 6 N hydrochloric acid and 4 mL of concentrated hydrochloric acid, and reacted and refluxed for 18 h. After concentration and chromatography on a silica gel column (CH$_3$OH:CH$_2$Cl$_2$=1:50), a light yellow solid was obtained. Recrystallization from methanol yielded 70 mg of 3-(4-(6-((1H-1,2,3-triazol-4-yl)amino)pyridin-3-yl)-3-fluorophenyl)-5-(hydroxylmethyl)oxazolidin-2-one, at a yield over two steps of 16.9%.

$^1$H NMR (DMSO-d$_6$) δ: 10.10 (br. s., 1H), 8.36 (s, 1H), 7.96-8.07 (m, 1H), 7.86 (m, 1H), 7.53-7.67 (m, 1H), 7.44 (m, 1H), 7.04-7.18 (m, 1H), 4.73 (m, 1H), 4.12 (m, 1H), 3.87 (m, 2H), 3.68 (m, 2H)

Compound 13 can be prepared according to the procedure for preparing Compound 13a above.

Example 13

Preparation of (R)-3-(3-fluoro-4-(2-((2-methyl-2H-tetrazol-5-yl)amino)thiazol-5-yl)phenyl)-5-(hydroxylmethyl)oxazolidin-2-one (Compound 14)

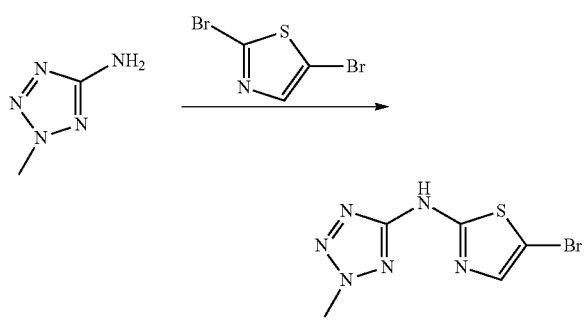

(1) Preparation of 5-bromo-N-(2-methyl-2H-tetrazol-5-yl)thiazol-2-amine

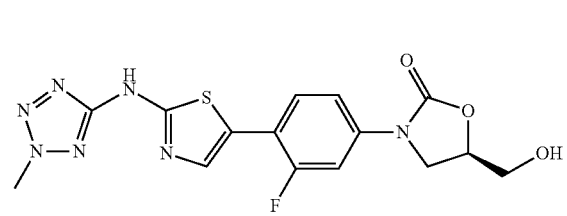 [SMILES: Cn1nnc(Nc2ncc(-c3ccc(N4C[C@H](CO)OC4=O)cc3F)s2)n1]

The procedure was the same as Example 1 (1) with the exception of using 2,5-dibromothiazole instead of 2-chloro-5-bromopyridine, at a yield of 27%.

(2) Preparation of tert-butyl(5-bromothiazol-2-yl(2-methyl-2H-tetrazol-5-yl))carbonate

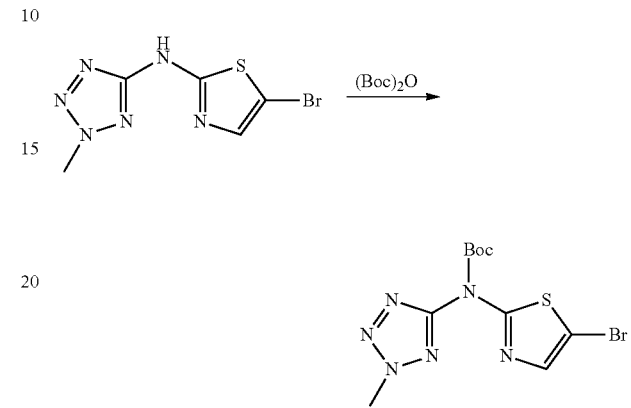

5-bromo-N-(2-methyl-2H-tetrazol-5-yl)thiazol-2-amine (0.7 g, 2.68 mmol) and triethylamine (0.8 mL, 5.72 mmol) were dissolved in 50 mL dichloromethane, and Boc$_2$O (0.7 g, 3.2 mmol) was added dropwise. The reaction was stirred at room temperature for 12 h. Water was added, extracted with ethyl acetate, and dried over anhydrous sodium sulfate. After concentration, 0.84 g of product was obtained, at a yield of 97%.

(3) Preparation of (R)-tert-butyl-5-(2-fluoro-4-(5-(hydroxylmethyl)-2-oxooxazolidin-3-yl)phenyl)thiazol-2-yl(2-methyl-2H-tetrazol-5-yl)carbonate

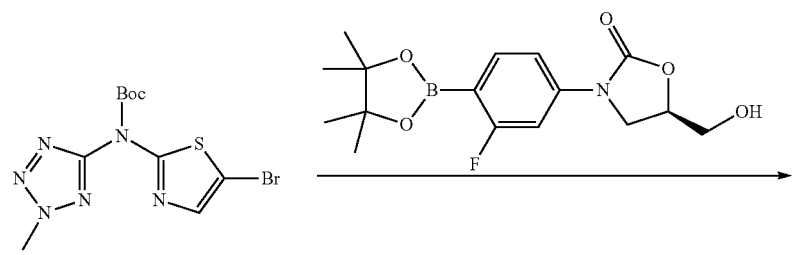

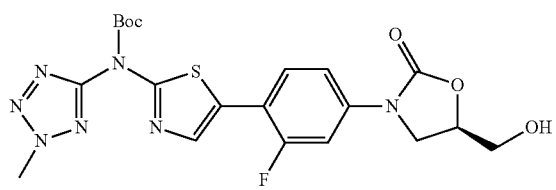

The procedure was the same as Example 1 (2) with the exception of using tert-butyl (5-bromothiazol-2-yl(2-methyl-2H-tetrazol-5-yl))carbonate instead of 5-bromo-N-(2-methyl-2H-tetrazol-5-yl)pyridine-2-amine, at a yield of 16%.

(4) Preparation of (R)-3-(3-fluoro-4-(2-((2-methyl-2H-tetrazol-5-yl)amino)thiazol-5-yl)phenyl)-5-(hydroxylmethyl)oxazolidin-2-one

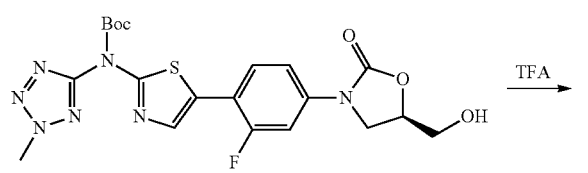

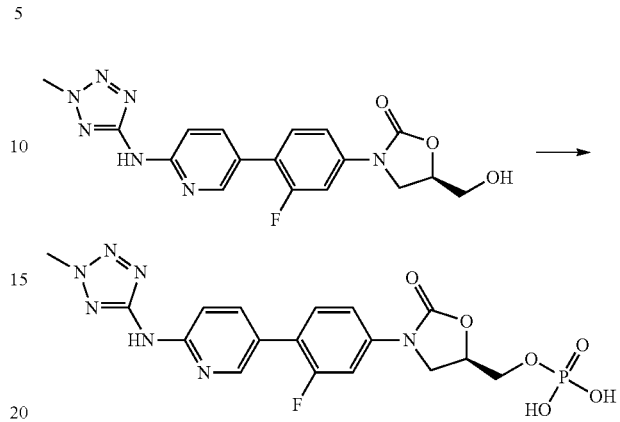

(R)-tert-butyl-5-(2-fluoro-4-(5-(hydroxylmethyl)-2-oxooxazolidin-3-yl)phenyl)thiazol-2-yl(2-methyl-2H-tetrazol-5-yl)carbonate (180 mg, 0.37 mmol) was dissolved in 30 mL dichloromethane, and TFA (0.4 mL, 5 mmol) was added. It was reacted at room temperature overnight. After concentration, the crude product was purified on a silica gel column (dichloromethane:methanol=20:1) to obtain 50 mg of (R)-3-(3-fluoro-4-(2-((2-methyl-2H-tetrazol-5-yl)amino)thiazol-5-yl)phenyl)-5-(hydroxylmethyl)oxazolidin-2-one.

Molecular formula: $C_{15}H_{14}FN_7O_3S$ Mass spectrum (m/e): 392.2 (M+1)

1H NMR (DMSO-d6): δ 12.07 (s, 1H), 7.72 (m, 2H), 7.63 (m, 1H), 7.40 (d, 1H), 5.23 (s, 1H), 4.73 (m, 1H), 4.31 (s, 3H), 4.10 (t, 1H), 3.85 (t, 1H), 3.68 (m, 1H), 3.56 (m, 1H)

Example 14

Preparation of (R)-3-(3-fluoro-4-(6-((2-methyl-2H-tetrazol-5-yl)amino)pyridin-3-yl)phenyl)-2-oxooxazolidin-5-yl)methyl phosphate disodium salt (Compound 2)

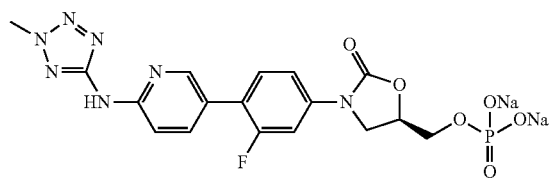

(1) Preparation of (R)-3-(3-fluoro-4-(6-((2-methyl-2H-tetrazol-5-yl)amino)pyridin-3-yl)phenyl)-2-oxooxazolidin-5-yl)methyl dihydrogen phosphate

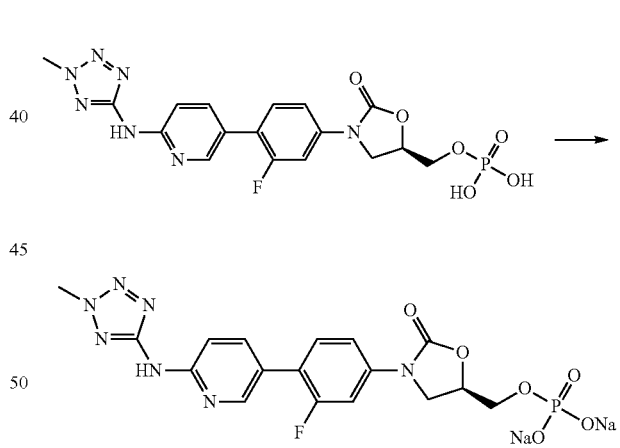

The procedure was the same as Example 4 (1) with the exception of using (R)-3-(3-fluoro-4-(6-((2-methyl-2H-tetrazol-5-yl)amino)pyridin-3-yl)phenyl)-5-(hydroxylmethyl)oxazolidin-2-one instead of (R)-3-(3-fluoro-4-(6-((1-methyl-1H-tetrazol-5-yl)amino)pyridin-3-yl)phenyl)-5-(hydroxylmethyl)oxazolidin-2-one.

(2) Preparation of (R)-(3-(3-fluoro-4-(6-(methyl(2-methyl-2H-tetrazol-5-yl)amino)pyridin-3-yl)phenyl)-2-oxooxazolidin-5-yl)methyl phosphate disodium salt The procedure was the same as Example 4 (2) with the exception of using (R)-3-(3-fluoro-4-(6-((2-methyl-2H-tetrazol-5-yl)amino)pyridin-3-yl)phenyl)-2-oxooxazolidin-5-yl)methyl dihydrogen phosphate instead of (R)-(3-(3-fluoro-4-(6-((1-methyl-1H-tetrazol-5-yl)amino)pyridin-3-yl)phenyl)-2-oxooxazolidin-5-yl)methyl dihydrogen phosphate.

Molecular formula: $C_{17}H_{15}FN_7Na_2O_6P$ Mass spectrum (m/e): 465.1 (M+1)

1H-NMR (400 MHz, DMSO): δ 7.98 (s, 1H), 7.51 (d, 1H), 7.06-7.17 (m, 2H), 6.96-7.00 (m, 2H), 4.75-4.82 (m, 1H), 4.12 (s, 3H), 3.81-3.96 (m, 4H)

The invention claimed is:

1. A compound of formula (I), a pharmaceutically acceptable salt thereof, or an isomer thereof,

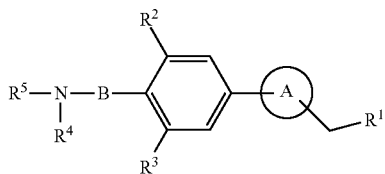

(I)

wherein,
R¹ is (1) —OR⁶, (2) —NR⁶R⁶', (3) —COR⁶, (4) —COOR⁶, (5) —OCOR⁶, (6) —CONR⁶R⁶', (7) —NR⁶COR⁶', (8) —OCONR⁶R⁶', (9) —NR⁶COOR⁶', (10) —NR⁶CONR⁶'R⁶, (11) —CSR⁶, (12) —CSOR⁶, (13) —OCSR⁶, (14) —CSNR⁶R⁶', (15) —NR⁶CSR⁶', (16) —OCSNR⁶R⁶', (17) —NR⁶CSOR⁶', (18) —NR⁶CSNR⁶'R⁶, (19) —NR⁶C(NR⁶)NR⁶'R⁶, (20) —S(O)$_p$R⁶, (21) —SO₂NR⁶R⁶', (22) R⁶, or (23) —OP(O)(OH)₂;
p is 0, 1, or 2;
R⁶ and R⁶' are independently (1) hydrogen, (2) C₁₋₆ alkyl, (3) C₂₋₆ alkenyl, (4) C₂₋₆ alkynyl, (5) —COC₁₋₆ alkyl, (6) —COC₂₋₆ alkenyl, or (7) —COC₂₋₆ alkynyl;
R² and R³ are independently hydrogen, halogen or C₁₋₆ alkyl;
A is

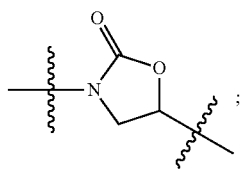 [SMILES: *C1CN(*)C(=O)O1]

B is

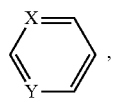

wherein X is C, Y is N;
R⁴ is (1) hydrogen, (2) C₁₋₆ alkyl, (3) C₂₋₆ alkenyl, (4) C₂₋₆ alkynyl, (5) —COC₁₋₆ alkyl, (6) —COC₂₋₆ alkenyl, or (7) —COC₂₋₆ alkynyl;
R⁵ is 1,2,3,4-tetrazolyl, unsubstituted or substituted by R⁷; and
R⁷ is halogen, carboxyl, hydroxyl, amino, cyano, nitro, C₁₋₆ alkyl, carboxyl C₁₋₆ alkyl, hydroxyl C₁₋₆ alkyl, amino C₁₋₆ alkyl, halo C₁₋₆ alkyl, C₁₋₆ alkoxyl, halo C₁₋₆ alkoxyl, C₁₋₆ alkoxyl C₁₋₆ alkyl, C₁₋₆ alkyl amino, di(C₁₋₆ alkyl)amino, di(C₁₋₆ alkyl)amino C₁₋₆ alkyl, C₁₋₆ alkyl carbonyl, C₁₋₆ alkyl carbonyloxy, C₁₋₆ alkoxyl carbonyl, carbamyl, carbamyl C₁₋₆ alkyl, C₁₋₆ alkyl carbamyl, di(C₁₋₆ alkyl)carbamyl, aminosulfonyl, aminosulfonyl C₁₋₆ alkyl, C₁₋₆ alkyl aminosulfonyl, di(C₁₋₆ alkyl)aminosulfonyl, C₁₋₆ alkyl sulfonylamino, C₁₋₆ alkyl sulfonyl, C₁₋₆ alkyl carbonylamino, or guanidino.

2. The compound of claim 1, a pharmaceutically acceptable salt thereof, or an isomer thereof, having a structure of the following formula (II):

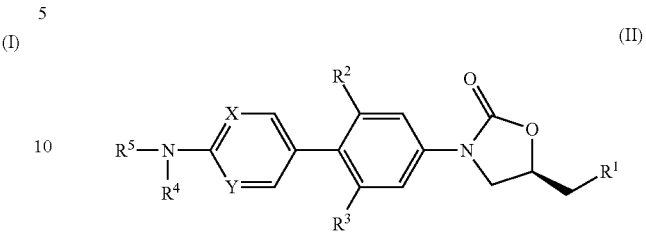

(II)

wherein, R¹, R², R³, R⁴, R⁵, X and Y are as defined in claim 1.

3. The compound of claim 1, a pharmaceutically acceptable salt thereof, or an isomer thereof,
wherein,
R¹ is —NHCOCH₃, —OH, —NH₂, —NHC₁₋₆ alkyl, or —OP(O)(OH)₂;
R² and R³ are independently hydrogen or halogen;
X is C and Y is N;
R⁴ is (1) hydrogen, (2) C₁₋₄ alkyl, (3) C₂₋₄ alkenyl, (4) C₂₋₄ alkynyl, (5) —C(O)C₁₋₄ alkyl, (6) —C(O)C₂₋₄ alkenyl, or (7) —C(O)C₂₋₄ alkynyl;
R⁵ is 1,2,3,4-tetrazolyl, unsubstituted or substituted by R⁷; and
R⁷ is halogen, carboxyl, hydroxyl, amino, cyano, nitro, C₁₋₄ alkyl, carboxyl C₁₋₄ alkyl, hydroxyl C₁₋₄ alkyl, amino C₁₋₄ alkyl, halo C₁₋₄ alkyl, C₁₋₄ alkoxyl, halo C₁₋₄ alkoxyl, C₁₋₄ alkoxyl C₁₋₄ alkyl, C₁₋₄ alkyl amino, di(C₁₋₄ alkyl)amino, di(C₁₋₄ alkyl)amino C₁₋₄ alkyl, C₁₋₄ alkyl carbonyl, C₁₋₄ alkyl carbonyloxy, C₁₋₄ alkoxyl carbonyl, carbamyl, carbamyl C₁₋₄ alkyl, C₁₋₄ alkyl carbamyl, di(C₁₋₄ alkyl)carbamyl, aminosulfonyl, aminosulfonyl C₁₋₄ alkyl, C₁₋₄ alkyl aminosulfonyl, di(C₁₋₄ alkyl)aminosulfonyl, C₁₋₄ alkyl sulfonylamino, C₁₋₄ alkyl sulfonyl, C₁₋₄ alkyl carbonylamino, or guanidino.

4. The compound of claim 3, a pharmaceutically acceptable salt thereof, or an isomer thereof,
wherein,
R¹ is —NHCOCH₃, —OH, or —OP(O)(OH)₂;
R² and R³ are independently hydrogen or halogen;
X is C, Y is N;
R⁴ is hydrogen or C₁₋₄ alkyl;
R⁵ is 1,2,3,4-tetrazolyl, unsubstituted or substituted by R⁷; and
R⁷ is C₁₋₄ alkyl or halo C₁₋₄ alkyl.

5. The compound of claim 4, a pharmaceutically acceptable salt thereof, or an isomer thereof,
wherein,
R¹ is —NHCOCH₃, —OH, or —OP(O)(OH)₂;
R² is hydrogen;
R³ is fluoro;
R⁴ is hydrogen or —CH₃;
X is C;
Y is N;
R⁵ is 1,2,3,4-tetrazolyl, unsubstituted or substituted by R⁷; and
R⁷ is C₁₋₄ alkyl or halo C₁₋₄ alkyl.

6. The compound of claim 5, a pharmaceutically acceptable salt thereof, or an isomer thereof,
wherein,
R⁵ is 1,2,3,4-tetrazolyl, unsubstituted or substituted by R⁷; and
R⁷ is C₁₋₄ alkyl.

7. The compound of claim 6, a pharmaceutically acceptable salt thereof, or an isomer thereof, the compound being:

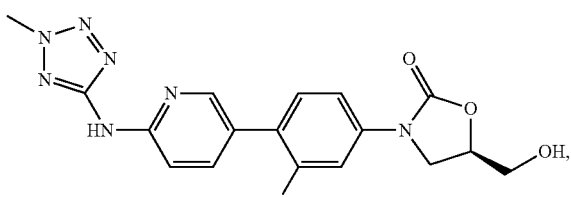

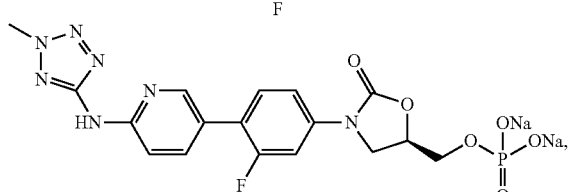

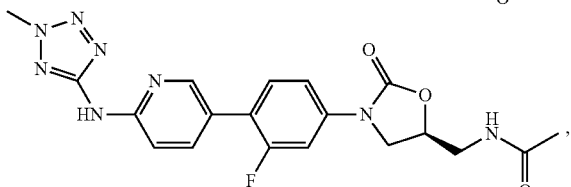

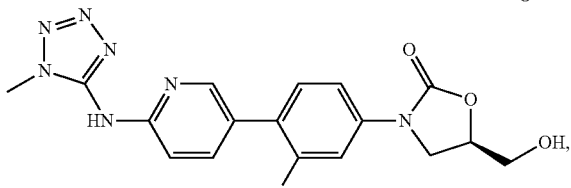

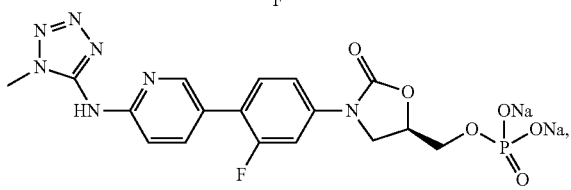

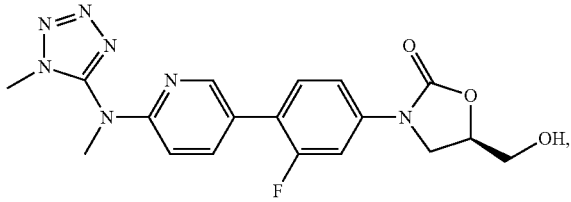

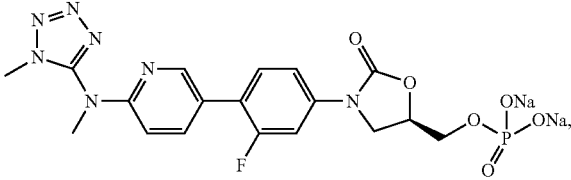

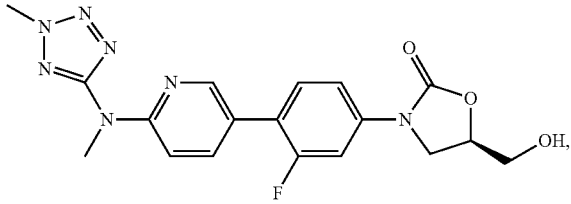

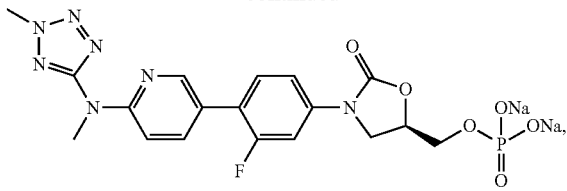

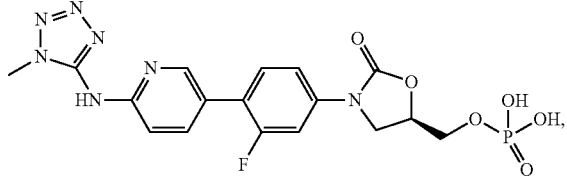

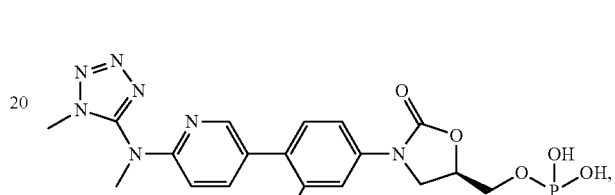

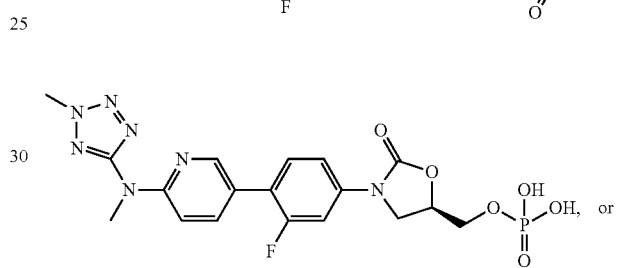

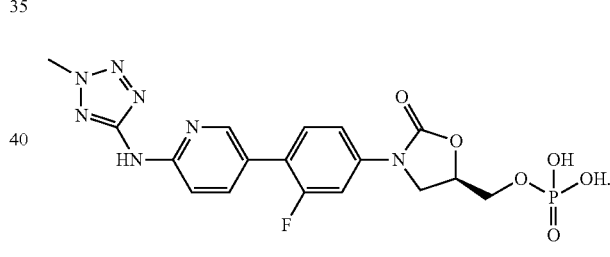

8. A pharmaceutical composition, comprising the compound of claim 1, a pharmaceutically acceptable salt thereof, or an isomer thereof, and one or more pharmaceutically acceptable carriers and/or diluents.

9. A method for treatment of an infectious disease caused by a Gram-positive bacteria, comprising administering to a subject in need thereof an effective amount of a compound of claim 1, a pharmaceutically acceptable salt thereof, or an isomer thereof, wherein the Gram-positive bacteria is methicillin-resistant *Staphylococcus aureus*, methicillin-sensitive *Staphylococcus aureus*, methicillin-resistant *Staphylococcus epidermidis*, methicillin-sensitive *Staphylococcus aureus*, *Enterococcus faecium*, *Enterococcus faecalis*, or *streptococcus pneumoniae*.

\* \* \* \* \*